(12) United States Patent
Nomura et al.

(10) Patent No.: US 6,703,345 B2
(45) Date of Patent: Mar. 9, 2004

(54) DIAZONIUM SALT AND HEAT-SENSITIVE RECORDING MATERIAL

(75) Inventors: Kimiatsu Nomura, Shizuoka-ken (JP); Tatsuo Kawabuchi, Shizuoka-ken (JP); Hisato Nagase, Shizuoka-ken (JP); Satoshi Higuchi, Shizuoka-ken (JP); Kimi Ikeda, Shizuoka-ken (JP); Yoshihiro Jinbo, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 146 days.

(21) Appl. No.: 10/132,292

(22) Filed: Apr. 26, 2002

(65) Prior Publication Data

US 2002/0183204 A1 Dec. 5, 2002

(30) Foreign Application Priority Data

Apr. 27, 2001 (JP) .......................... 2001-132424

(51) Int. Cl.⁷ ............................. B41M 5/26; B41M 5/30
(52) U.S. Cl. ......................... 503/218; 503/215; 534/558
(58) Field of Search .................... 534/558; 503/218, 503/215

(56) References Cited

FOREIGN PATENT DOCUMENTS

| JP | 4-59288 | 2/1992 |
|---|---|---|
| JP | 4-197782 | 7/1992 |
| JP | 4-201483 | 7/1992 |
| JP | 7-96671 | 4/1995 |
| JP | 7-125446 | 5/1995 |
| JP | 7-223367 | 8/1995 |
| JP | 7-223368 | 8/1995 |
| JP | 7-323660 | 12/1995 |
| JP | 8-244342 | 9/1996 |
| JP | 9-156229 | 6/1997 |
| JP | 9-216468 | 8/1997 |
| JP | 9-216469 | 8/1997 |
| JP | 9-319023 | 12/1997 |
| JP | 9-319025 | 12/1997 |
| JP | 10-35113 | 2/1998 |
| JP | 10-193801 | 7/1998 |
| JP | 10-264532 | 10/1998 |
| JP | 10-337961 | 12/1998 |
| JP | 11-105432 | 4/1999 |
| JP | 11-342675 | 12/1999 |
| JP | 2000-15935 | 1/2000 |
| JP | 2002326981 A | * 11/2002 |

* cited by examiner

*Primary Examiner*—N. Edwards
(74) *Attorney, Agent, or Firm*—Sughrue Mion, PLLC

(57) ABSTRACT

The present invention provides a diazonium salt represented by the following general formula (1) wherein $R^1$ represents a branched alkyl group; $R^2$ and $R^3$ separately represent an alkyl group and may bond to each other to form a ring; $R^4$, $R^5$, and $R^6$ separately represent a hydrogen atom, an alkyl group, or an aryl group and $R^4$ and $R^5$ may bond to each other to form a ring; and $X^-$ represents an anion and a heat-sensitive recording material comprising a heat-sensitive recording layer including the diazonium salt and a coupler.

General formula (1)

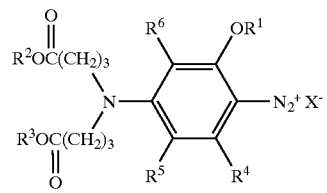

20 Claims, No Drawings

DIAZONIUM SALT AND HEAT-SENSITIVE RECORDING MATERIAL

BACKGROUND OF THE INVENTION

1. Field of the Invention

The present invention relates to a diazonium salt, which is important as an synthesis intermediate of an azo dye, an analytical reagent or a constituent material of a heat-sensitive recording material and to a heat-sensitive recording material containing a diazonium salt and a coupler as coloring components and more particularly to a diazonium salt which has no probability of explosion and high storage stability and which results in little stain formation by decomposition and to a heat-sensitive recording material with excellent storage property before printing (raw storage property) and the light-resistance after printing (image storage property).

2. Description of the Related Art

A diazonium salt is known as an important intermediate of an azo dye. A variety of synthesis methods of the azo dye is known and, as described in "New Experimental Chemistry Lecture" (published by Maruzen Co., Ltd., vol. 14-III, pp. 1516–1534), examples thereof include synthesis methods by oxidation reaction, reduction reaction, substitution reaction, addition reaction, condensation reaction, and the like. However, the industrial production method of the azo dye which is widely employed is a synthesis method by azo coupling of a diazonium with a coupler such as aniline, a phenol or the like in terms of the availability of raw materials, the cost, the production yield and the like. Such a method has a risk in which explosion of the diazonium salt may occur during the synthesis process. Consequently, it has been required to develop a stable diazonium salt with little possibility of explosion.

Further, the diazonium salt, as described in Japanese Patent Application Laid-Open (JP-A) No. 11-228517, is used for quantitative analysis of bilirubin, a main component of a bile pigment contained in the body fluid, and regarded as an important compound in the medical and pharmaceutical fields.

The diazonium salt is generally an extremely chemically active compound and easily reacts with a compound having a phenol derivative and an active methylene group so-called coupler to form an azo dye and is also photosensitive and decomposes when exposed to light and loses its activity. Accordingly, the diazonium salt has been utilized in an optical recording material such as diazo copying ("Basis of Photographic-Engineering-Non-Silver Halide Photography", edited by Japan Photography Associate, published by Corona, 1982, pp. 89–117, pp. 182–201).

Further, nowadays, based on the characteristic in which the diazonium salt decomposes when exposed to light and loses the activity, it is employed in a recording material which requires image fixation and a typical example is a photo-fixation type heat-sensitive recording material proposed in "Journal of Imaging Electronics Associate", vol. 11, no. 4, 1982, pp. 290–296 (Koji Sato, et al.) It has a recording layer containing the diazonium salt and a coupler and is heated according to image signals so as to cause a reaction of the components contained in the material and so as to form an image and then is exposed to light in order to fix the formed image.

Such a recording material containing the diazonium salt as a coloring component has a disadvantage in which the diazonium salt gradually thermally decomposes even in a dark place since the diozonium salt has an extremely high chemical activity and thus the non-image areas are colored by production of the colored substances by the decomposition and the contrast of the image is decreased. Further, it has another disadvantage in which the image after recording fades under sunlight or light of a fluorescent lamp.

A variety of means for improving such instability of the diazonium salt have been proposed. One of the most efficient means is a method of encapsulating the diazonium salt in microcapsules. Since the diazonium salt is isolated from substances such as water and a base which promote decomposition by encapsulating the diazonium salt, decomposition of the diazonium salt can considerably be suppressed and the shelf-life of a recording material in which the method is employed can remarkably be prolonged (Tomomasa Usami, et al., "Journal of Electrophotography Associate", vol. 26, no. 2, 1987, pp. 115–125).

A general method for encapsulating the diazonium salt in microcapsules is a method for producing microcapsules by steps of dissolving the diazonium salt in a hydrophobic solvent (an oil phase); adding the oil phase to an aqueous solution containing a water-soluble polymer (a water phase); carrying out emulsification and dispersion by a homogenizer or the like; and polymerizing monomers or a prepolymer included in the oil phase and/or the water phase at the interface to form or deposit a polymer which composes the wall of the microcapsules. Such a method is described in details, for example, in "Microcapsule" (written by Tomoji Kondo, published by The Nikkan Kogyo Shimbun, Ltd. 1970), "Microcapsule" (written by Tamotsu Kondo, et al., Sankyo Shuppan, 1977) and the like. As the material of the capsule wall, cross-linked gelatin, an alginic acid salt, cellulose, urea resin, urethane resin, melamine resin, nylon resin and the like can be used.

In particular, microcapsules having a glass transition temperature slightly higher than a room temperature such as urea resin and urethane resin prevents a substance from permeating the capsule wall at room temperature and allows the substance to pass through the wall at a temperature equal to or higher than the glass transition temperature, so that they are called thermally responsive microcapsules and are extremely useful for heat-sensitive type recording materials. That is, in the case of a heat-sensitive recording material comprising a heat-sensitive recording layer containing thermally respondensive microcapsules containing a diazonium salt and outside of the microcapsules a coupler as coloring components, the diazonium salt can be maintained stably for a long time and a color image can easily be formed by heating it and the formed image can be fixed by light radiation.

To encapsulate the diazonium salt can remarkably improve the stability of a recording material.

Although the stability of a recording material is remarkably improved as described above, instability due to the diazonium salt itself is not completely suppressed and coloration of non-image areas after a long term storage of the recording material is not sufficiently suppressed. Also, there still remains a problem that an image fades even after printing and fixing the image if it is exposed for a long time to a light source.

Present inventors have proposed a variety of diazonium salts as diazo compounds suitable for recording materials (JP-A Nos. 1-80588, 4-59288, 4-197782, 6-328853, 8-31033, 10-337961, 11-105432, 11-342675, and 2000-15935), however depending on the storage conditions of the recording materials, coloration may take place and thus further improvement is required in order to obtain stable images with high grades. On the other hand, lightfastness of images after printing and fixing is insufficient.

SUMMARY OF THE INVENTION

The present invention aims to solve the above-described conventional problems and achieve the following objects.

That is, the objects of the invention are at first to provide a diazonium salt with no probability of explosion, useful for a synthesis intermediate of an azo dye, an analytical reagent, or a constituent material for a heat-sensitive recording material, having a stable storage property, and with little stain formation and secondary to provide a heat-sensitive recording material capable of giving an image which is free from coloration in non-image areas with the lapse of time during storage and thus excellent in whiteness and also scarcely fades when exposed to sunlight, light from a fluorescent lamp or the like and thus excellent in lightfastness.

A first aspect of the invention is a diazonium salt represented by the following general formula (1): General formula (1)

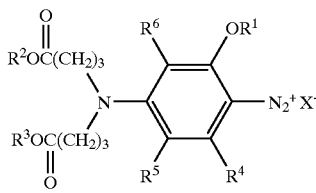

wherein $R^1$ represents a branched alkyl group; $R^2$ and $R^3$ separately represent an alkyl group and may bond to each other to form a ring; $R^4$, $R^5$, and $R^6$ separately represent a hydrogen atom, an alkyl group, or an aryl group and $R^4$ and $R^5$ may bond to each other to form a ring; and $X^-$ represents an anion.

A second aspect of the invention is a heat-sensitive recording material comprising a support and a heat-sensitive recording layer including the foregoing diazonium salt and a coupler.

DETAILED DESCRIPTION OF THE PREFERRED EMBODIMENTS

Hereinafter, the present invention will be described in detail.

I. Diazonium salt

A diazonium salt of the present invention is a compound represented by the general formula (1). The compound, as shown below, is a benzenediazonium salt having a branched alkoxyl at 2-position and di(alkoxycarbonylpropyl)amino group at 4-position and due to the structure, the diazonium salt itself is stable, free from occurrence of coloring stains by photodecomposition, can maintain the whiteness, is excellent in the lightfastness after coloration, and further has no probability of explosion. General formula (1)

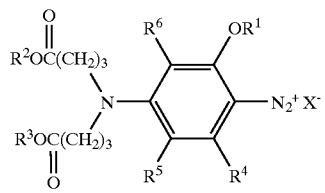

In the general formula (1), $R^1$ represents a branched alkyl group.

The branched alkyl represented by $R^1$ may be unsubstituted or substituted group and the substituent, if any, is preferably, for example, a phenyl group, a halogen atom, an alkoxy group, an aryloxy group, an alkoxycarbonyl group, an acylamino group, a carbamoyl group, a cyano group, an alkylsulfonyl group, an arylsulfonyl group, a sulfonamido group, a sulfamoyl group, acyl group, a heterocyclic group or the like.

The branched alkyl group is preferably an alkyl group having 3 to 30 carbon atoms; more preferably an alkyl group having 3–15 carbon atoms and examples thereof include 2-propyl group, 2-butyl group, 2-methylpropyl group, 2-pentyl group, 3-pentyl group, 2,2-dimethylpropyl group, 3-methylbutyl group, 2-hexyl group, 4-methylpentyl group, 2-octyl group, 2-ethylhexyl group, 3,5,5-trimethylhexyl group, 2-butyloctyl group, 2-hexyldecyl group, 2-phenoxypropyl group, 2-(4-methoxyphenoxy)propyl group and the like.

Among them, 2-methylpropyl group, 3-pentyl group, 2,2-dimethylpropyl group, 3-methylbutyl group, 2-ethylhexyl group, 3,5,5-trimethylhexyl group, 2-butyloctyl group, and 2-hexyldecyl group are preferable.

$R^2$ and $R^3$ separately represent an alkyl. The alkyl group may be unsubstituted or substituted and the substituent group, if any, is preferably, for example, a phenyl group, a halogen atom, an alkoxy group, an aryloxy group, an alkoxycarbonyl group, an acylamino group, a carbamoyl group, a cyano group, an alkylsufonyl group, an arylsulfonyl group, a sulfonamido group, sulfamoyl group, acyl group, or a heterocyclic group.

The alkyl represented by $R^2$, $R^3$ is preferably an alkyl group having 1–10 carbon atoms; more preferably an alkyl group having 1 to 4 carbon atoms and examples thereof include methyl group, ethyl group, propyl group, 2-propyl group, butyl group, 2-butyl group, pentyl group, 2-methoxyethyl group, 2-ethoxyethyl group, 2-propoxyethyl group, 2-butoxyethyl group and the like.

Among them, methyl group, ethyl group, propyl group, 2-propyl group, and butyl group are preferable.

Further, $R^2$, $R^3$ may bond to each other to form a ring and in this case, an alkylene group, an arylene group, a polyethyleneoxy group are preferable as $R^2$ or $R^3$ and among them, ethylene group, propylene group, and phenylene group are more preferable.

$R^4$, $R^5$, and $R^6$ separately represent a hydrogen atom, an alkyl group, or an aryl group.

The alkyl group represented by $R^4$, $R^5$ and $R^6$ may be unsubstituted or substituted and the substituent group, if any, is, for example, a phenyl group, a halogen atom, an alkoxy group, an aryloxy group, an alkoxycarbonyl group, an acylamino group, a carbamoyl group, a cyano group, an alkylsufonyl group, an arylsulfonyl group, a sulfonamido group, sulfamoyl group, acyl group, or a heterocyclic group.

The alkyl group represented by $R^4$, $R^5$ and $R^6$ is preferably an alkyl group having 1 to 20 carbon atoms; more preferably an alkyl group having 1 to 10 carbon atoms and examples thereof include methyl group, ethyl group, propyl group, isopropyl group, butyl group, 1,1-dimethylethyl group, hexyl group, octyl group, 2-ethylhexyl group, 3,5,5-trimethylhexyl group, dodecyl group, cyclohexyl group, benzyl group, a-methylbenzyl group, allyl group, 2-chloroethyl group, 2-methoxyethyl group, 2-ethoxyethyl group, 2-phenoxyethyl group, 2-(2,5-di-tert-amylphenoxy) ethyl group, 2-benzoyloxyethyl group, methoxycarbonylmethyl group, methoxycarbonylethyl group, butoxycarbonylethyl group, 2-isopropyloxyethyl group, 2-methanesulfonylethyl group, 2-ethoxycarbonylmethyl group, 1-(4-methoxyphenoxy)-2-propyl group, trichloromethyl group, and trifluoromethyl group.

Among them, methyl group, ethyl group, propyl group, benzyl group, 2-methoxethyl group, and 2-ethoxyethyl group are preferable.

The aryl represented by $R^4$, $R^5$ and $R^6$ may be unsubstituted or substituted and the substituent group, if any, is, for example, a phenyl group, a halogen atom, an alkoxy group, an aryloxy group, an alkoxycarbonyl group, an acyloxy group, an acylamino group, a carbamoyl group, a cyano group, an alkylsufonyl group, an arylsulfonyl group, a sulfonamido group, a sulfamoyl group, an acyl group, and a heterocyclic group.

The aryl represented by $R^4$, $R^5$ and $R^6$ is preferably an aryl group having 6 to 30 carbon atoms; more preferably an aryl group having 6 to 12 carbon atoms and examples thereof include phenyl group, 4-methylphenyl group, 3-methylphenyl group, 2-methylphenyl group, 4-chlorophenyl group, 2-chlorophenyl group, 4-nitrophenyl group, 4-acetamidophenyl group, 4-octanoylaminophenyl group, 4-(4-methylphenylsulfonylamino)phenyl group, and naphthyl group.

Among them, phenyl group, 4-methylphenyl group, and 4-chlorophenyl group are preferably and phenyl group and 4-methylphenyl group are more preferable.

$R^4$ and $R^5$ may bond to each other to form a ring and in this case, $R^4$ or $R^5$ is preferably an alkylene group, an arylene group, a polyethylene oxy group, and a benzo condensed ring. Among them, butylene and a benzo condensed ring are preferable.

$X^-$ represents an anion. The anion may be an inorganic anion or an organic anion.

The inorganic anion is preferably, for example, hexafluorophosphoric acid ion, borofluoric acid ion, chloride ion, sulfic acid ion, and among them, hexfluorophosphoric acid ion and borofluoric acid ion are especially preferable. Further, the organic anion is preferably, for example, a polyfluoroalkylcarboxylic acid ion, a polyfluoroalkylsulfonic acid ion, tetrafphenylboric acid ion, an aromatic carboxylic acid ion, and an aromatic sulfonic acid ion and among them, polyfluoroalkylsulfonic acid ion, tetraphenylboric acid ion, and the aromatic carboxylic acid ion are especially preferable.

$R^4$, $R^5$ and $R^6$ is most preferably a hydrogen atom. That is, among the diazonium salt represented by the foregoing general formula (1), the diazonium salt represented by the following general formula (2) is preferable. The diazonium salt with such a structure has the maximum absorption wavelength of about 370 nm and can easily decompose when exposed to ultraviolet rays. General formula (2)

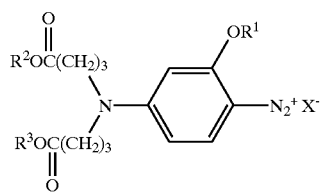

In the general formula (2), $R^1$ represents a branched alkyl group and the branched alkyl group can be the same as $R^1$ of the above-described general formula (1) and its preferable examples are also the same. Further, $R^2$ and $R^3$ separately represent an alkyl group and the alkyl group is also the same as those of $R^2$ and $R^3$ of the above-described general formula (1) and their preferable examples are also the same. $X^-$ represents an anion and the anion is the same as $X^-$ of the general formula (1) and its preferable examples are also the same.

In the diazonium salts represented by the foregoing general formula (1) or (2), at least one of $R^1$, $R^2$, $R^3$, $R^4$, $R^5$ and $R^6$ may have a diazoaryl group as a substituent group and may form a bis- or higher polymer unit.

Hereinafter, specific examples (exemplified compounds A-1 to A-24) of the diazonium salt represented by the general formula (1) or (2) are as follows, however the diazonium salt of the present invention is not restricted to these examples.

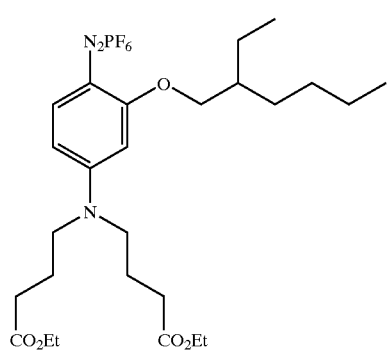

A-1

-continued
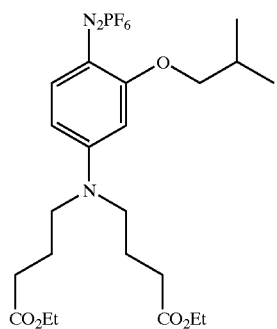
A-2
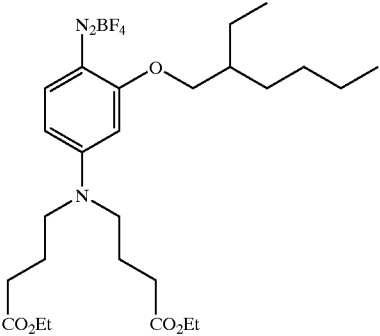
A-7
A-3
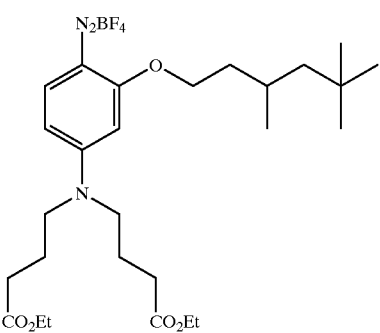
A-8
A-4
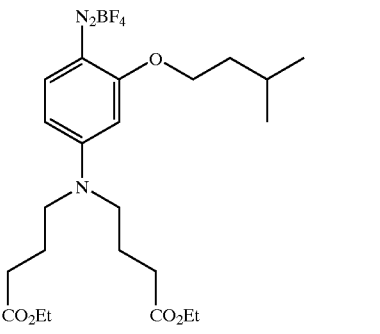
A-9
A-5
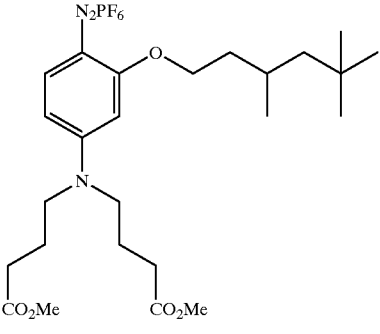
A-10
A-6

A-11
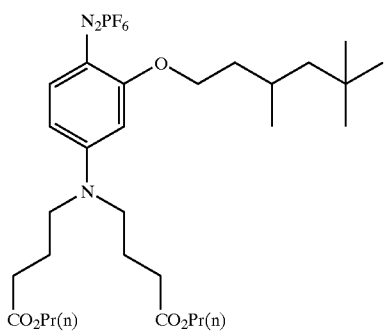
A-12
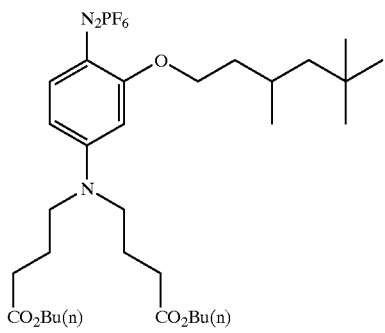
A-13
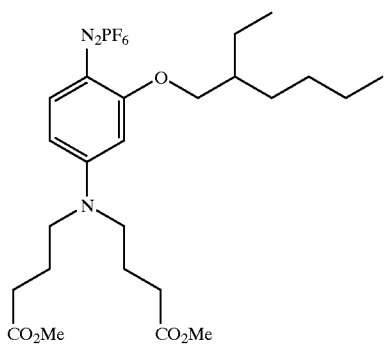
A-14
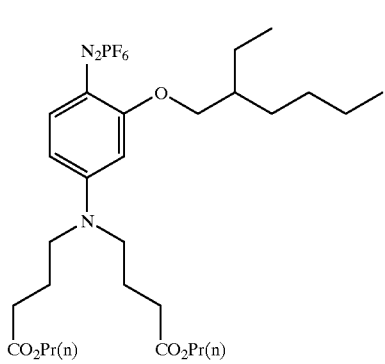
A-15
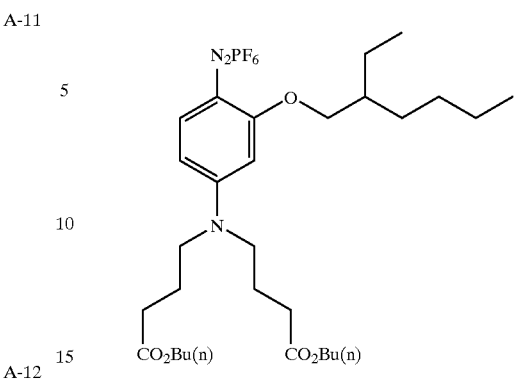
A-16
A-17
A-18

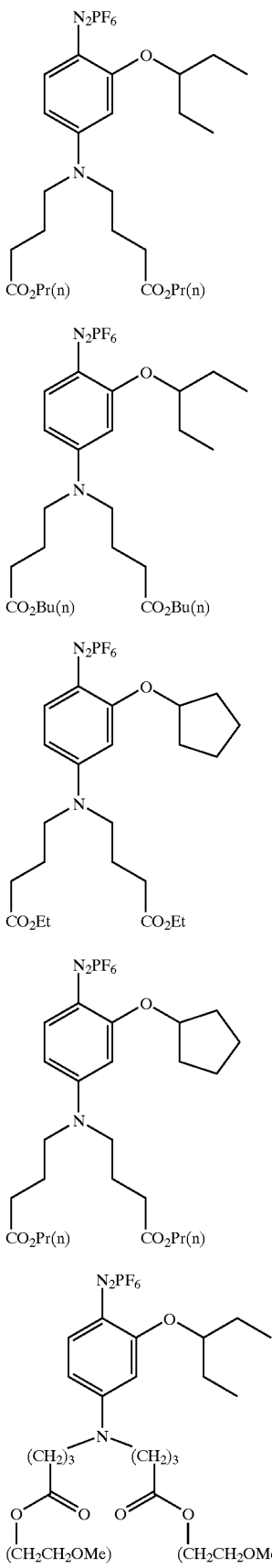

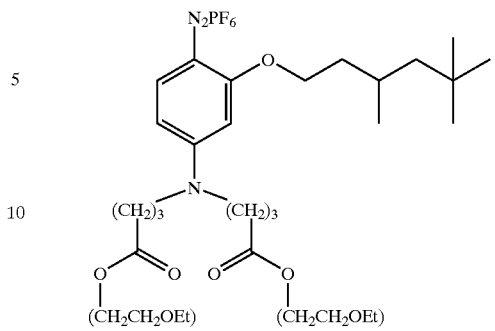

Further, the diazonium salt represented by the general formula (1) or (2) can be produced by a known method. That is, it can be obtained by converting corresponding aniline into a diazo compound in an acidic solvent using sodium nitrite, nitrosyl sulfate, isoamyl sulfite and the like.

Further, the diazonium salt represented by the general formula (1) or (2) may be oily or crystalline state, yet from a viewpoint of the handling easiness, those in crystalline state at a normal temperature are preferable. These diazonium salts may be used alone or as a mixture of two or more of them, or may be used together with another diazonium salt.

In the case of adding such a diazonium salt to a heat-sensitive recording layer of a heat-sensitive recording material as it will be described later, the content is preferably 0.02 to 5 g/m$^2$ and more preferably 0.1 to 4 g/m$^2$ in terms of the coloring density.

In order to stabilize the diazonium salt of the present invention, a complex compound may be formed using zinc chloride, cadmium chloride, tin chloride or the like.

The diazonium salt represented by the general formula (1) or (2) is reacted with a coupler which will be described later, forms color and gives a high coloring density with excellent color forming property and the resultant dye is excellent in lightfastness. Further, the diazonium salt is excellent in the photo decomposability when exposed to light of fluorescent lamp with a wavelength ranging from 350 to 430 nm, has quick decomposability enough to complete the fixation sufficiently by light radiation within a short time, and scarcely causes coloration (stain occurrence) by photo decomposition, so that it is extremely suitable for a coloring component to be used in a photo-fixation type heat-sensitive recording material and can form an image with excellent durability, whiteness of background and a high contrast.

II. Heat-sensitive recording material

A heat-sensitive recording material of the present invention comprises at least one heat-sensitive recording layer on the surface of a support and may further comprise other layer such as a protection layer, an intermediate layer and the like, if necessary.

Heat-sensitive recording layer

A heat-sensitive recording layer contains at least one diazonium salt and at least one coupler to be reacted with the diazonium salt and preferably contains an organic base and may further contain other components, if necessary.

Diazonium salt

In the present invention, at least one diazonium salt of the present invention represented by the general formula (1) or (2) is contained and the details of the diazonium salt are as described already.

Coupler

A coupler (a coupling component) usable for the heat-sensitive recording material of the present invention will be described.

As the coupler, any compound can be used if it forms a dye by coupling with a diazonium salt in a basic atmosphere and/or a neutral atmosphere. So-called 4-equivalent couplers for silver halide photosensitive materials can be used as the coupler. They may be selected corresponding to the aimed hue. Examples thereof include so-called active methylene compound having a methylene group next to a carbonyl group, a phenol derivative, a naphthol derivative and the like and these compounds are properly selected and used so that the purpose of the invention is satisfied.

The examples of the coupler are resorcin, phloroglucin, 2,3-dihydroxynaphthalene, sodium 2,3-dihydroxynaphthalene-6-sulfonate, 1-hydroxy-2-naphthoic acid morpholinopropylamide, sodium 2-hydroxy-3-naphthalenesulfonate, 2-hydroxy-3-naphthalenesulfonic acid anilide, 2-hydroxy-3-naphthalenesulfonic acid morpholinopropylamide, 2-hydroxy-3-naphthalenesulfonic acid-2-ethylhexyloxypropylamide, 2-hydroxy-3-naphthalenesulfonic acid-2-ethylhexylamide, 5-acetamido-1-naphthol, sodium 1-hydroxy-8-acetamidonaphthalene-3,6-disulfonate, 1-hydroxy-8-acetamidonaphthalene-3,6-disulfonic acid dianilide, 1,5-dihydroxynaphthalene, 2-hydroxy-3-naphthoic acid morpholinopropylamide, 2-hydroxy-3-naphthoic acid octylamide, 2-hydroxy-3-naphthoic acid anilide, 5,5-dimethyl-1,3-cyclohexanedione 1,3-cyclopentanedione, 5-(2-n-tetradecyloxyphenyl)-1,3-cyclohexanedione, 5-phenyl-4-methoxycarbonyl-1,3-cyclohexanedione, 5-(2,5-di-n-octyloxyphenyl)-1,3-cyclohexanedione, N,N-dicyclohexylbarbituric acid, N,N'-di-n-dodecylbarbituric acid, N-n-octyl-N'-n-octadecylbarbituric acid, N-phenyl-N'-(2,5-di-n-octyloxydiphenyl)barbituric acid, N,N'-bis(octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamido-5-pyrazolone, 6-hydroxy-4-methyl-3-cyano-1-(2-ethylhexyl)-2-pyridone, 2,4-bis(benzoylacetamido)toluene, 1,3-bis(pivaloylacetamidomethyl)benzene, benzoylacetonitrile, thenoylacetonitrile, acetoacetoanilide, benzoylacetoanilide, pivaloylacetoanilide, 2-chloro-5-(N-n-butylsulfamoyl)-1-pivaloylacetamidobenzene, 1-(2-ethylhexyloxypropyl)-3-cyano-4-methyl-6-hydroxy-1,2-dihydropyridine-2-one, 1-(dodecyloxypropyl)-3-acetyl-4-methyl-6-hydroxy-1,2-dihydropyridine-2-one, 1-(4-n-octyloxyphenyl)-3-tert-butyl-5-aminopyrazole and the like.

Details of the couplers are described in JP-A Nos. 4-201483, 7-223367, 7-223368, 7-323660, Japanese Patent Application Nos. 5-278608, 5-297024, 6-18669, 6-18670, 7-316280, 8-027095, 8-027096, 8-030799, 8-12610, 8-132394, 8-358755, 8-358756, 9-069990 and the like.

Among the couplers described above, a compound or its tautomers represented by the following general formula (3) are preferable.

General formula (3)

In the general formula (3), $E^1$ and $E^2$ separately represent an electron attractive group and $E^1$ and $E^2$ may bond with each other to form a ring.

The electron attractive groups represented by $E^1$ or $E^2$ mean substituent groups with a positive $\sigma_p$ value of Hammett and they may be the same as or different from each other and examples thereof include an acyl group such as acetyl group, propionyl group, pivaloyl group, chloroacetyl group, trichloroacetyl group, trifluoroacetyl group, 1-methylcyclopropylcarbonyl group, 1-ethylcyclopropylcarbonyl group, 1-benzylcyclopropylcarbonyl group, benzoyl group, 4-methoxybenzoyl group, thenoyl group, and the like; an oxycarbonyl such as methoxycarbonyl group, ethoxycarbonyl group, 2-methoxyethoxycarbonyl group, 4-methoxyphenoxylcarbonyl group, and the like; a carbamoyl such as carbamoyl group, N,N-dimethylcarbamoyl group, N,N-diethylcarbamoyl group, N-phenylcarbamoyl group, N-[2,4-bis(pentyloxy)phenyl]carbamoyl group, N-[2,4-bis(octyloxy)phenyl]carbamoyl group, morpholinocarbonyl and the like; an alkylsulfonyl or an arylsulfonyl such as methanesulfonyl group, benzenesulfonyl group, toluenesulfonyl and the like; a phosphono group such as diethylphosphono group; a heterocyclic group such as benzoxazol-2-yl group, benzothiazol-2-yl group, 3,4-dihydroquinazolin-4-one-2-yl group, 3,4-dihydroquinazoline-4-sulfon-2-yl and the like; a nitro group; an imino group; a cyano group and the like.

Further, the electron attractive groups represented by $E^1$ or $E^2$ may bond with each other to form a ring and the ring to be formed is preferably a 5-member or 6-member carbocyclic ring or hetero ring.

Further, among the compounds represented by the general formula (3), the compounds represented by the following general formula (4) are especially preferable. General formula (4)

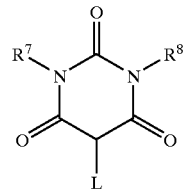

In the general formula (4), $R^7$ and $R^8$ separately represent a hydrogen atom, an alkyl group, or an aryl group.

The alkyl group represented by $R^7$ and $R^8$ may be unsubstituted or substituted and in the case of a substituted alkyl, the substituent group is, for example, phenyl group, a halogen atom, an alkoxy group, an aryloxy group, an alkoxycarbonyl group, an acyloxy group, an acylamino group, a carbamoyl group, a cyano group, an alkylsulfonyl group, an arylsulfonyl group, a sulfonamido group, a sulfamoyl group, acyl group, a heterocyclic group and the like.

The alkyl represented by R7 or $R^8$ is preferably an alkyl group having 1–30 carbon atoms; more preferably an alkyl group having 10–25 carbon atoms and examples thereof include methyl group, ethyl group, propyl group, isopropyl group, butyl group, 1,1-dimethylethyl group, hexyl group, octyl group, 2-ethylhexyl group, 3,5,5-trimethylhexyl group, dodecyl group, cyclohexyl group, benzyl group, a-methylbenzyl group, allyl group, 2-chloroethyl group, 2-methoxyethyl group, 2-ethoxyethyl group, 2-phenoxyethyl group, 2-(2,5-di-tert-amylphenoxy)ethyl group, 3-octyloxypentyl group, 2-benzoyloxyethyl group, methoxycarbonylmethyl group, ethoxycarbonylmethyl group, methoxycarbonylethyl group, butoxycarbonylethyl group, octyloxycarbonylmethyl group, octadecyloxycarbonyl group, 2-isopropyloxyethyl group, 2-methanesulfonylethyl group, 1-(4-methoxyphenoxy)-2-propyl group, trichloromethyl group, and trifluoromethyl group.

Among them, 2-ethylhexyl, 3,5,5-trimethylhexyl, 2-(2,5-di-tert-amylphenoxy)ethyl, 2-benzoyloxyethyl, methoxycarbonylmethyl, ethoxycarbonylmethyl, methoxycarbonylethyl, butoxycarbonylethyl, octyloxycarbonylmethyl, octadecyloxycarbonyl, 2-isopropyloxyethyl, 1-(4-methoxyphenoxy)-2-propyl are preferable.

The aryl group represented by $R^7$ or $R^8$ may be unsubstituted or substituted and the substituent group in the case of a substituted group is preferably, for example, an alkyl group, a phenyl group, a halogen atom, an alkoxy group, an aryloxy group, an alkoxycarbonyl group, an acyloxy group, an acylamino group, a carbamoyl group, a cyano group, an alkylsufonyl group, an arylsulfonyl group, a sulfonamido group, sulfamoyl group, acyl group, and a heterocyclic group.

The aryl represented by $R^7$ or $R^8$ is preferably an aryl group having 1–30 carbon atoms, more preferably an aryl group having 10–25 carbon atoms and examples thereof include phenyl group, 2-methylphenyl group, 3-methylphenyl group, 4-methylphenyl group, 2-phenylphenyl group, 4-phenylphenyl group, 2-chlorophenyl group, 4-chlorophenyl group, 4-bromophenyl group, 2-methoxyphenyl group, 2-butoxyphenyl group, 2-(2-ethylhexyloxy)phenyl group, 3-hexyloxyphenyl group, 4-ethoxyphenyl group, 4-hexyloxyphenyl group, 4-(3,5,5-trimethylhexyloxy)phenyl group, 2-phenoxyphenyl group, 4-phenoxyphenyl group, 2-methoxycarbonylphenyl group, 4-ethoxycarbonylphenyl group, 3-butoxycarbonylphenyl group, 2-acetamidophenyl group, 4-acetamidophenyl group, 4-cyanophenyl group, 2-octylsulfonylphenyl group, 4-octylsulfonylphenyl group, 2-dibutylaminocarbamoylphenyl group, 4-dibutylaminocarbamoylphenyl group, 4-cyclohexylphenyl group, 2,5-dioctyloxyphenyl group, 2,4-dihexyloxyphenyl group, and 2,3-dimethoxyphenyl group.

Among them, phenyl group, 2-methylphenyl group, 3-methylphenyl group, 4-methylphenyl group, 2-chlorophenyl group, 4-chlorophenyl group, 2-methoxyphenyl group, 2-butoxyphenyl group, 2-(2-ethylhexyloxy)phenyl group, 3-hexyloxyphenyl group, 4-ethoxyphenyl group, 4-hexyloxyphenyl group, 4-(3,5,5-trimethylhexyloxy)phenyl group, 2-methoxycarbonylphenyl group, 4-ethoxycarbonylphenyl group, 3-butoxycarbonylphenyl group, 2-acetamidophenyl group, 4-acetamidophenyl group, 2-dibutylaminocarbamoylphenyl group, 4-dibutylaminocarbamoylphenyl group, 4-cyclohexylphenyl group, 2,5-dioctyloxyphenyl group, and 2,4-dihexyloxyphenyl group are preferable.

L of the general formula (4) represents a hydrogen atom or a substituent group capable of dissociating when the coupler is coupled with a diazonium salt (hereinafter, simply referred to as a leaving group).

Only one or two or more leaving groups may be introduced as substituent groups into the compound represented by the general formula (4). The leaving groups may be a halogen atom, an aromatic azo group, or an alkyl group, an aryl group, a heterocyclic group, an alkylsulfonyl group, an arylsulfonyl group, an arylsulfinyl group, an alkylcarbonyl group, an arylcarbonyl group, or a heterocyclic carbonyl group to be bonded to the coupling site through an oxygen, nitrogen, sulfur or carbon atom, or a heterocyclic group to be bonded to the coupling site through a nitrogen atom.

Examples of the groups are a halogen atom, an alkoxy group, an aryloxy group, an acyloxy group, an alkylsulfonyloxy group, an arylsulfonyloxy group, an acylamino group, an alkylsulfonamido group, an arylsulfonamide group, an alkoxycarbonyloxy group, an aryloxycarbonyloxy group, an alkylthio group, an arylthio group, a heterocyclic thio group, a carbamoylamino group, an arylsulfinyl group, an arylsulfonyl group, a 5-membered or 6-membered nitrogen-containing heterocyclic group, an imide group, an arylazo group and the like, and the alkyl group and the heterocyclic group contained in these leaving groups may further substituted with a substituent group such as an alkoxy group, an aryloxy group, a halogen atom, an alkoxycarbonyl group, an alkylcarbonyloxy group and the like.

Further, as the leaving group, an amino group, an ether group, and a thio ether group to be bonded to the coupling site through a carbon atom are also exemplified and more particularly, dimethylaminomethyl group, hydroxymethyl group, ethoxymethyl group, phenoxymethyl group, methylthioxymethyl group, phenylthioxymethyl group, and the like can be exemplified.

In the case two or more substituent groups are introduced, the substituent groups may be the same as or different from one another and these substituent groups may have the above exemplified substituent groups. Further, the leaving group may form a ring with a coupler mother nucleus.

That is practically as follows. The halogen atom is, for example, fluorine, bromine, chlorine, and iodine; the alkoxy group is, for example, ethoxy group, dodecyloxy group, methoxyethylcarbamoylmethoxy group, carboxypropyloxy group, methylsulfonylethoxy group, ethoxycarbonylmethoxy, and the like; the aryloxy group is, for example, 4-methylphenoxy group, 4-chlorophenoxy group, 4-methoxyphenoxy group, 4-carboxyphenoxy group, 3-ethoxycarboxyphenoxy group, 3-acetylaminophenoxy group, 2-carboxyphenoxy group, and the like; the acyloxy group is, for example, acetoxy group, tetradecanoyloxy group, benzoyloxy group and the like; the alkylsulfonyloxy group or arylsulfonyloxy group is, for example, methanesulfonyloxy group, toluenesulfonyloxy group, and the like; the acylamino group is, for example, dichloroacetylamino group, heptafluorobutyrylamino group and the like; the alkylsulfonamido group or arylsulfonamido group is, for example, methanesulfonamido group, trifluoromethanesulfonamido, p-toluenesulfonylamido and the like.

The alkoxycarbonyloxy group is, for example, ethoxycarbonyloxy group, benzyloxycarbonyloxy group, and the like; the alkylthio group, arylthio group or heterocyclic thio group is, for example, ethylthio group, 2-carboxyethylthio group, dodecylthio group, 1-carboxydodecylthio group, phenylthio group, 2-butoxy-tert-octylphenylthio group, tetrazolylthio group and the like; the arylsulfonyl group is, for example, 2-butoxy-tert-octylphenylsulfonyl and the like; and the arylsulfinyl is, for example, 2-butoxy-tert-octylphenylsulfinyl group and the like. The carbamoylamino group is, for example, N-methylcarbamoylamino, N-phenylcarbamoylamino, and the like; the 5-membered or 6-membered nitrogen-containing heterocyclic group is, for example, imidazolyl, pyrazolyl, triazolyl, tetrazolyl, 1,2-dihydro-2-oxo-1-pyridyl, and the like; the imido group is, for example, succinimide, hydantoin, and the like; and the arylazo group is, for example, phenylazo, 4-methoxyphenylazo, and the like. These groups may further be substituted.

Hereinafter, specific examples (exemplified compounds (B-1) to (B-44)) of the coupler represented by the general formula (3) or (4) are shown, however the coupler of the invention is not at all restricted to these compounds.

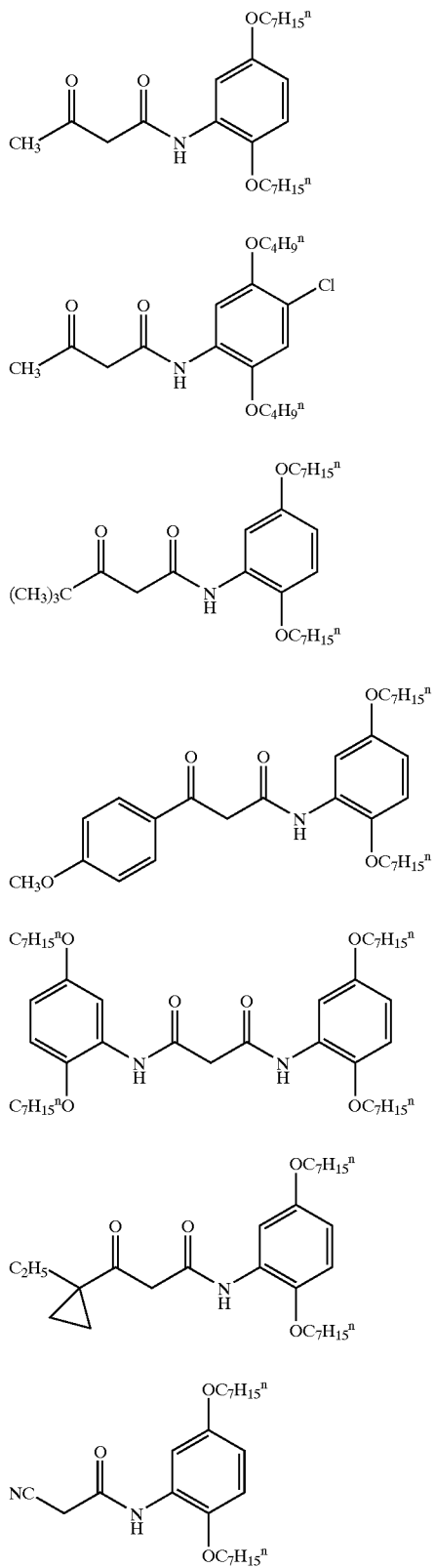
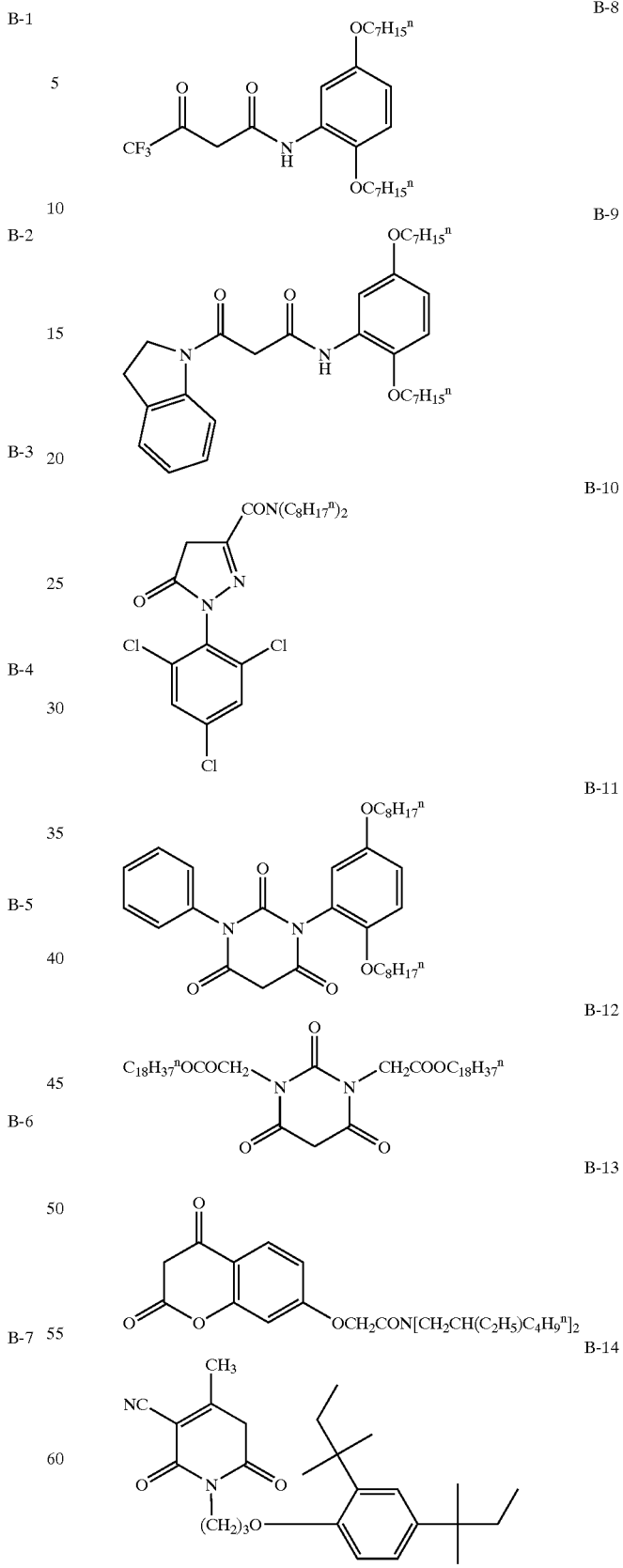

-continued

B-15 through B-22, B-23 through B-28: chemical structures.

-continued
B-29
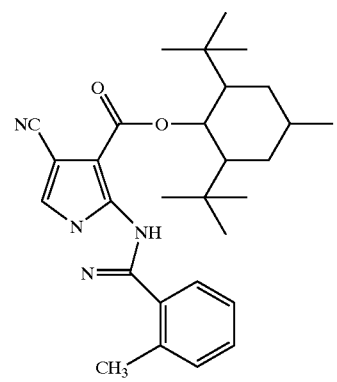
B-30
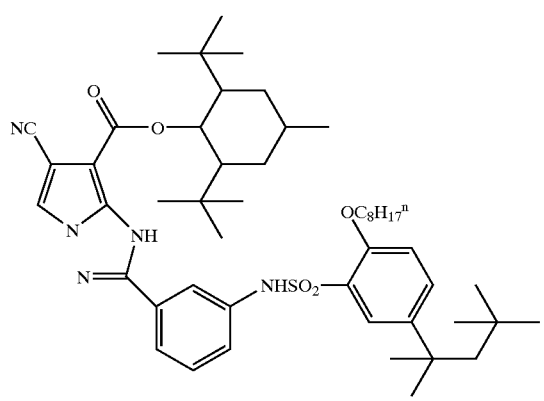
B-31
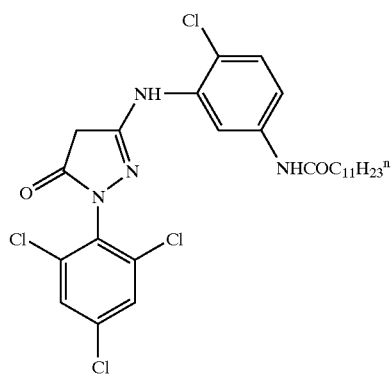
B-32
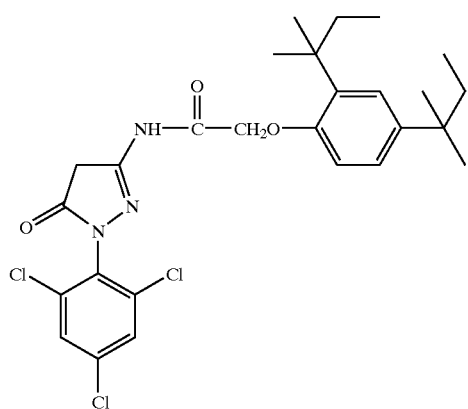
-continued
B-33
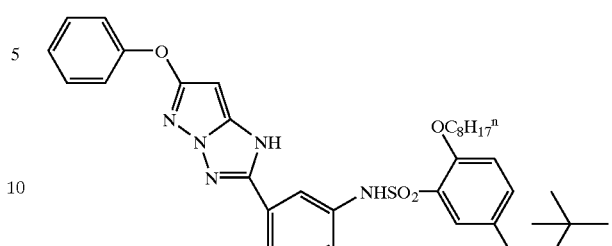
B-34
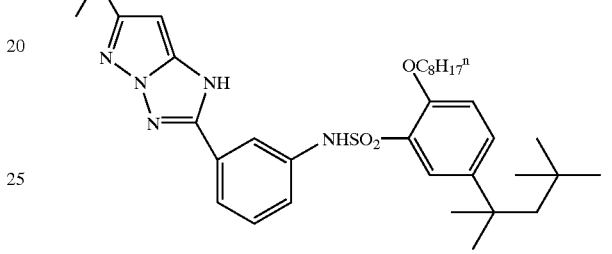
B-35
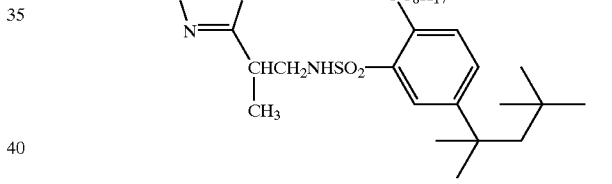
B-36
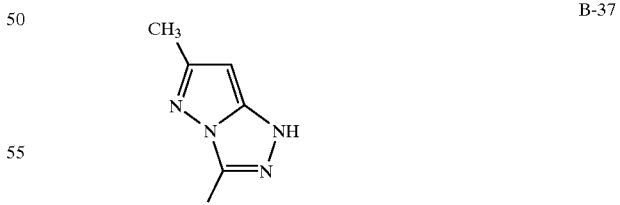
B-37

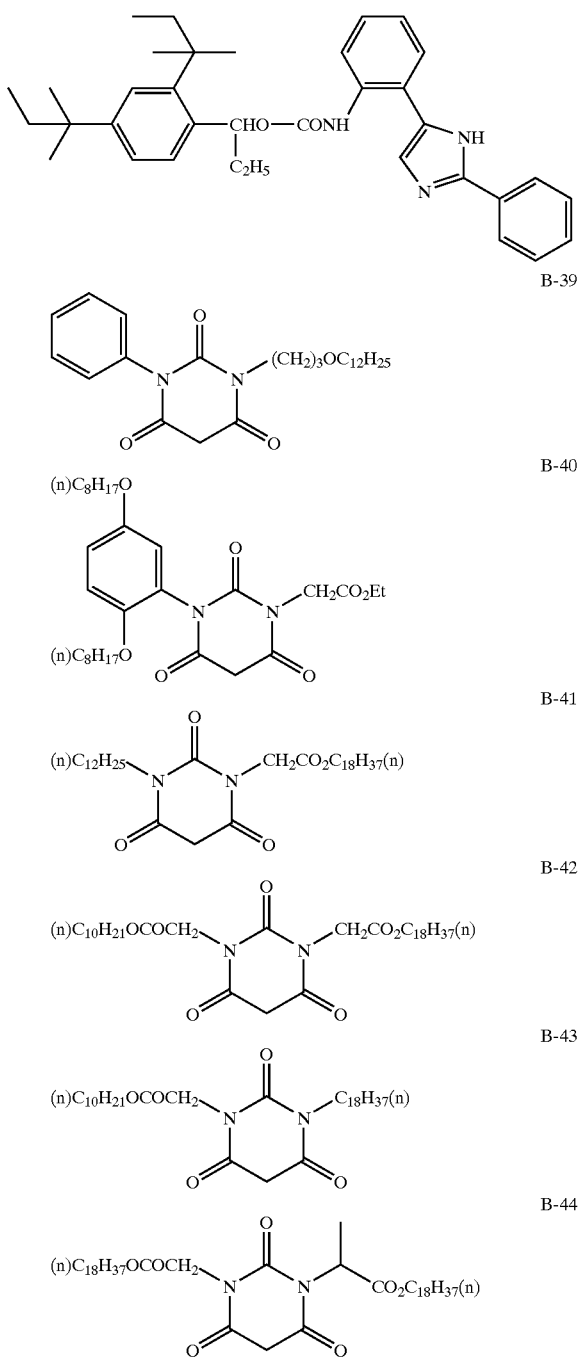

The tautomers of the couplers mean isomers of the exemplified couplers which isomers have structures easy to be converted to the couplers and such tautomers are also preferable as the coupler employed in the invention.

Micro capsulation

In a heat-sensitive recording material of the present invention, for the purpose of improvement of the raw storage property before the use, it is preferable to encapsulate a diazonium salt in microcapsules. The method of forming the microcapsule may properly be selected from known methods, as described above.

As a polymer substance for forming the capsule wall of the microcapsules, it is required to inhibit a substance from permeating the wall at a normal temperature and allow it to permeate the wall at the time of heating, so that those having a glass transition temperature of 60 to 200° C. are preferable and, for example, a polyurethane, a polyurea, a polyamide, a polyester, a urea-formamide resin, a melamine resin, a polystyrene, styrene-methacrylate copolymer, a styrene-acrylate copolymer, and their mixture can be exemplified.

As a microcapsule formation method, specifically, an interfacial polymerization method and an internal polymerization method are suitable. The details of the capsule formation method and specific examples of reactants are described in U.S. Pat. Nos. 3,726,804, 3,796,669, and the like. For example, in the case a polyurea and a polyurethane are used as a capsule wall material, polyisocyanate and a second substances (for example, a polyol and a polyamine) for forming the capsule wall by reaction with the polyisocyanate are mixed with an aqueous solvent or an oil-based solvent to be encapsulated, emulsified in water and then heated to cause polymer formation reaction in the interfaces of the oil droplets and form the microcapsule wall. In the case of omitting the second substances, a polyurea can also be produced.

In the present invention, as the polymer substance for forming the capsule wall of the microcapsule, it is preferable to contain at least one kind of polymers (e.g., a polyurethane, a polyurea and the like) containing urethane and/or urea as constituent components.

Next, a production method of a diazonium salt-encapsulating microcapsule (a polyurea-polyurethane wall) will be described.

At first, a diazonium salt is dissolved or dispersed in a hydrophobic organic solvent to produce an oil phase to which will be cores of the microcapsules. In this case, a poly-functional isocyanate as a wall material is also added to the oil phase.

At the time of producing the oil phase, as the hydrophobic organic solvent to dissolve or disperse the diazonium salt therein, an organic solvent having a boiling point ranging from 100 to 300° C. is preferable and more specifically, an alkylnaphthalene, an alkyldiphenylethane, an alkyldiphenylmethane, an alkylbiphenyl, an alkylterphenyl, chlorinated paraffin, phosphoric acid esters, maleic acid esters, adipic acid esters, phthalic acid esters, benzoic acid esters, carbonic acid esters, ethers, sulfuric acid esters, sulfonic acid esters, and the like can be exemplified. They may be used as a mixture of two or more of them.

In the case in which the solubility of the diazonium salt to be encapsulated in the organic solvent is low, a low boiling point solvent in which the diazonium salt to be employed has a high solubility may be used in combination for an auxiliary use and the low boiling point solvent is, for example, ethyl acetate, propyl acetate, isopropyl acetate, butyl acetate, methylene chloride, tetrahydrofuran, acetonitrile, acetone and the like.

Hence, the diazonium salt preferably has a proper solubility in a high boiling point hydrophobic organic solvent and a low boiling point solvent and more specifically, it is preferable to have a solubility of 5% or higher to the respective solvents. The solubility in water is preferably 1% or lower.

On the other hand, an aqueous solution in which the water-soluble polymer is dissolved is used as the water phase and after addition of the oil phase, emulsification is carried out by a means such as a homogenizer and at that time, the water-soluble polymer is useful for uniformly and easily carrying out the dispersion and works as a dispersant to stabilize the emulsified aqueous solution. In this case, in order to carry out uniform emulsification and stabilize the emulsion, a surfactant may be added to at least one of the oil phase and the water phase. As the surfactant, known surfactants for emulsification are usable. The addition amount in the case of adding a surfactant is preferably 0.1 to 5% by weight, more preferably 0.5 to 2% by weight, to the weight of the oil phase.

A water-soluble polymer is preferably a water-soluble polymer with a solubility of 5% or higher in water at a temperature at which emulsification is to be carried out and, for example, polyvinyl alcohol and its modified products, polyacrylic acid amide and it derivatives, an ethylene-vinyl acetate copolymer, a styrene-maleic acid anhydride copolymer, an ethylene-maleic anhydride copolymer, isobutyrene-maleic acid anhydride copolymer, polyvinylpyrolidone, ethylene-acrylic acid copolymer, vinyl acetate-acrylic acid copolymer, carboxymethyl cellulose, methyl cellulose, casein, gelatin, starch derivatives, gum arabic, sodium alginate and the like can be exemplified.

The water-soluble polymer is preferably non-reactive or scarcely reactive with an isocyanate compound and, for example, those having a reactive amino group in a molecular chain such as gelatin is preferably converted to be non-reactive ones by modification or the like before mixing.

The poly-functional isocyanate compound is preferably a compound having a tri- or higher-functional isocyanate group or may be a compound having a bifunctional isocyanate group. More specifically, examples of such compounds are dimers or trimers (beret, or isocyanurate) in which the main raw material is a diisocyanate such as xylenediisocyanate and its hydrates, hexamethylenediisocyanate and its hydrates, tolylenediisocyanate and its hydrates, isophoronediisocyanates, and the like; poly-functional adducts of polyols such as trimethylolpropane and bi-functional isocyanates such as xylylenediisocyanate; those produced by introducing a high molecular weight compounds such as polyethers having active hydrogen such as polyethylene oxide into adducts of polyols such as trimethylolpropane and bi-functional isocyanates such as xylylenediisocyanate; and formalin condensates of benzeneisocyanate.

Among them, compounds described in JP-A Nos. 62-212190, 4-26189, 5-317694, Japanese Patent Application No. 8-268721 and the like are preferable.

The use amount of a poly-functional isocyanate is so determined as to control the average particle diameter of the microcapsules to be 0.3 to 12 $\mu$m and the wall thickness to be 0.01 to 0.3 $\mu$m. Also, the dispersion particle diameter is generally about 0.2 to 10 $\mu$m.

In an emulsified dispersion produced by adding the oil phase to the water phase, a polyurea wall is formed by polymerization reaction of poly-functional isocyanate occurring in the interface of the oil phase and the water phase.

If a polyol and/or a polyamine is added in the water phase or the hydrophobic solvent of the oil phase, it can be utilized as one of constituent components of the microcapsule wall obtained by reaction with the poly-functional isocyanate. In the reaction, it is preferable to keep the reaction temperature high or add a proper polymerization catalyst in terms of acceleration of the reaction speed.

Specific examples of the polyol or the polyamine are propylene glycol, glycerin, trimethylolpropane, triethanolamine, sorbitol, hexamethylenediamine and the like. In the case of adding the polyol, a polyurethane wall is formed.

The poly-functional isocyanate, polyol, reaction catalyst, or polyamine for composing some of the wall-forming agent are described in details in a book (Polyurethane Handbook, IWATA Keiji, Nikkan Kogyo Shimbun, 1987).

Emulsification can be carried out using properly selected known emulsifying apparatuses such as a homogenizer, a Manthon gully, a ultrasonic dispersing apparatus, a dissolver, a Keddy mill and the like. After emulsification, in order to promote the capsule wall formation reaction, the resulting emulsion is heated to 30 to 70° C. Further, in order to prevent agglomeration of each capsule from others during the reaction, it is required to add water to lower the collision probability of the capsules or sufficiently stir the emulsion.

Further, a dispersant for preventing agglomeration may be added during the reaction. Along with the proceeding of the polymerization reaction, carbon dioxide gas evolution is observed and at the time of finishing the evolution, the capsule wall formation reaction can be assumed to finish. Generally, the reaction for several hours makes it possible to obtain an aimed microcapsules encapsulating the diazonium salt.

A coupler may be solid-dispersed with, for example, a water-soluble polymer, an organic salt, and other coloring assisting agent by a sand mill or the like, however the coupler is preferably used in form of an emulsified dispersion produced by dissolving it in a high boiling point organic solvent which is hardly soluble or insoluble in water, mixing the resulting solution with an aqueous polymer solution (a water phase) containing a surfactant and/or a water-soluble polymer as a protective colloid, and emulsifying the obtained mixture by a homogenizer or the like. In this case, if necessary, a low boiling point solvent may also be used as a dissolution assisting agent. Further, the coupler and the organic base may either separately be emulsified or be mixed together at first and then dissolved in a high boiling point organic solvent and emulsified. The preferable emulsified dispersion particle diameter is 1 $\mu$m or smaller.

The use amount of the coupler is preferably 0.1 to 30 parts by weight to 1 part by weight of the diazonium salt.

The high boiling point organic solvent to be used in this case can properly be selected, for example, among the high boiling point oils described in JP-A No. 2-141279. Above all, from a viewpoint of the stability of the emulsified dispersion, esters are preferable and tricresyl phosphate is especially preferable. The oils or mixtures with other oils are also usable.

To the organic solvent, further an auxiliary solvent with a low boiling point may be added as a dissolution assisting solvent and preferable examples of the assisting solvent are ethyl acetate, isopropyl acetate, butyl acetate, methylene chloride and the like. In some cases, no high boiling point oil is added and only an assisting solvent with a low boiling point may be used.

Further, the water-soluble polymer to be added as a protection colloid to the water phase may properly be selected from known anionic polymers, nonionic polymers, and amphoteric polymers and among them, for example, polyvinyl alcohol, gelatin, cellulose derivatives and the like are preferable.

Further, the surfactant to be added to the water phase is an anionic or nonionic surfactant and may properly be selected from those which do not react on the protection colloid and do not precipitate or agglomerate. The surfactant is, for example, sodium alkylbenzenesulfonate, sodium alkylsulfate, dioctyl sodium sulfosuccinate, polyalkylene glycol (e.g., polyoxyethylene nonylphenyl ether) and the like.

Organic base

In the present invention, an organic base is preferably added as a basic substance to promote the coupling reaction of the diazonium salt and the coupler.

Examples of the organic salt are nitrogen-containing compounds such as tertiary amines, piperidines, piperazines, amidines, formamidines, pyridines, guanidines, morpholines and the like and preferable ones are exemplified, for example, in Japanese Patent Application Publication (JP-B) No. 52-46806, JP-A Nos. 62-70082, 57-169745, 60-94381, 57-123086, 60-49991, JP-B Nos. 2-24916, 2-28479, JP-A Nos. 60-165288, 57-185430. They may be used alone or as a mixture of two or more of them.

Among those described above, practically preferable ones are piperazines such as N,N'-bis(3-phenoxy-2-hydroxypropyl)piperazine, N,N'-bis[3-(p-methylphenoxy)-2-hydroxypropyl]piperazine, N,N'-bis[3-(p-methoxyphenoxy)-2-hydroxypropyl]piperazine, N,N'-bis(3-phenylthio-2-hydroxypropyl)piperazine, N,N'-bis[3-(β-naphthoxy)-2-hydroxypropyl]piperazine, N-3-(β-naphthoxy)-2-hydroxypropyl-N'-methylpiperazine, 1,4-bis{[3-(N-methylpiperazino)-2-hydroxy]propyloxy}benzene, and the like; morpholines such as N-[3-(β-naphthoxy)-2-hydroxy]propylmorpholine, 1,4-bis(3-morpholino-2-hydroxy-propyloxy)benzene, 1,8-bis(3-morpholino-2-hydroxy-propyloxy)benzene, and the like; piperidines such as N-(3-phenoxy-2-hyroxypropyl)piperidine, N-dodecylpiperidine and the like; and guanidines such as triphenylguanidine, tricyclohexylguanidine, dicyclohexylphenylguanidine and the like.

The use amount of the organic base is preferably 0.1 to 30 parts by weight to 1 part by weight of the diazonium salt.

If the use amount is less than 0.1 parts by weight, sufficient coloring density cannot be obtained in some cases and if it is more than 30 parts by weight, decomposition of the diazonium salt is promoted in some cases.

Other component

Further, to the heat-sensitive recording layer, other than the above described organic base, an agent for promoting the color forming reaction, that is, a coloring assisting agent, may also be added for the purpose of fast and complete thermal printing with low energy. In this case, the coloring assisting agent is a substance for increasing the coloring density during thermal recording or controlling the coloring temperature, and for lowering the melting point of the coupler, the basic substance, or the diazonium salt or lowering the softening point of the capsule wall to simplify the reactions of a diazonium salt, a basic substance, a coupler and the like.

The coloring assisting agent is, for example, phenol derivatives, naphthol derivatives, alkoxy-substituted benzenes, alkoxy-substituted naphthalenes, aromatic ethers, thio ethers, esters, amides, ureides, urethanes, sulfonamide compounds, hydroxy compounds and the like.

The coloring assisting agent includes a thermofusible substance. The thermofusible substance is a substance which has a melting point ranging from 50 to 150° C. and is solid at a normal temperature and melted by heating and capable of dissolving a diazonium salt, a coupler, or an organic base therein. More specifically, examples of the agent are carboxylic acid amides, N-substituted carboxylic acid amide, ketone compounds, urea compounds, and esters.

In a heat-sensitive recording material of the present invention, for the purpose to improve the fastness of thermally colored image to light and heat or for the purpose to lessen the yellowing of unprinted areas (non-image areas) by light after fixation.

Antioxidants disclosed in European Patent Application Nos. 223739, 309401, 309402, 310551, 310552, 459416, Germany Patent No. 3435443, JP-A Nos. 54-48535, No. 62-262047, 63-113536, 63-163351, 2-262654, 2-71262, 3-121449, 5-61166, 5-119449, U.S. Pat. Nos. 4,814,262, 4,980,275 and the like can be preferably used.

It is also effective to use various known additives which have already been known in a heat-sensitive or pressure sensitive recording material.

As the various additives, the compounds disclosed in JP-A Nos. 60-107384, 60-107383, 60-125470, 60-125471, 60-125472, 60-287485, 60-287486, 60-287487, 60-287488, 61-160287, 61-185483, 61-211079, 62-146678, 62-146680, 62-146679, 62-282885, 63-051174, 63-89877, 63-88380, 63-088381, 63-203372, 63-224989, 63-251282, 63-267594, 63-182484, 1-239282, 4-291685, 4-291684, 5-188687, 5-188686, 5-110490, 5-170361, JP-B Nos. 48-043294, 48-033212 and the like can be used.

More specifically, 6-ethoxy-1-phenyl-2,2,4-trimethyl-1,2-dihydroquinoline, 6-ethoxy-1-octyl-2,2,4-trimethyl-1,2-dihydroquinoline, 6-ethoxy-1-phenyl-2,2,4-trimethyl-1,2,3,4-tetrahydroquinoline, 6-ethoxy-1-octyl-2,2,4-trimethyl-1,2,3,4-tetrahydroquinoline, nickel cyclohexanate, 2,2-bis(4-hydroxyphenyl)propane, 1,1-bis(4-hydroxyphenyl)-2-ethylhexane, 2-methyl-4-methoxy-diphenylamine, 1-methyl-2-phenylindole and the like can be exemplified The addition amount of the antioxidant or other various additives is preferably 0.05 to 100 parts by weight, more preferably 0.2 to 30 parts by weight, to 1 part by weight of the diazonium salt.

The antioxidant and various additives may be added to the microcapsule together with the diazonium salt, or may be added as the solid dispersion together with the coupler, the basic substance, and another coloring assisting agent, or may be added to the emulsion together with proper emulsification assisting agents; or may be added in both states. Further, the antioxidant or the various additives may be used alone or in combination of a plurality of them. Moreover, they may be added to the protection layer.

The antioxidant and various additives are not necessary to added to the same layer.

In the case in which the antioxidant and/or various additives are used in combination of a plurality of them, they may be classified based on the structure into anilines, alkoxybenzenes, hindered phenols, hindered amines, hydroquinones, phosphorus compounds, and sulfur compounds and combined with those with different structures or combined with a plurality of those with the same structures.

For the purpose of lessening the yellowing of the background texture portions after the image recording, a free radical-generating agent (a compound to generate a free radical by light radiation) which is employed in a photopolymerization composition and the like can be added.

As the free radical-generating agent, for example, aromatic ketones, quinones, benzoins, benzoin ethers, azo compounds, organic disulfides, acyloxime esters and the like can be exemplified.

The addition amount of the free radical-generating agent is preferably 0.01 to 5 parts by weight to 1 part by weight of the diazonium salt.

Further, for the purpose of lessening the yellowing, a polymerizable compound having an ethylenic unsaturated bond (hereinafter, referred to as vinyl monomer) may be used. The vinyl monomer is a compound having at least one ethylenic unsaturated bond (vinyl, vinylidene and the like) in the chemical structure and having a chemical form of a monomer or prepolymer.

The vinyl monomer is, for example, an unsaturated carboxylic acid and its salts, esters of unsaturated carboxylic acids and aliphatic polyhydric alcohols, and amides of unsaturated carboxylic acids and aliphatic polyvalent amine compounds. The vinyl monomer is used in a range from 0.2 to 20 parts by weight to 1 part by weight of the diazonium salt.

The free radical-generating agent and vinyl monomer may be enclosed together with the diazonium salt in the microcapsules.

Further, as an acid stabilizer, citric acid, tartaric acid, oxalic acid, boric acid, phosphoric acid, pyrophosphoric acid and the like may also be added.

The method of applying a coating solution for heat-sensitive recording layer formation can be selected from known coating methods such as, a bar coating, a blade coating, an air knife coating, a gravure coating, a roll coating, a spraying coating, a dip coating, a curtain coating methods.

The coating amount of the heat-sensitive recording layer after coating and drying is preferably 2.5 to 30 $g/m^2$.

The constitution of the heat-sensitive recording layer of the heat-sensitive recording material of the present invention is not particularly restricted and may be, for example, a monolayer in which the microcapsules, the coupler, and the organic base are all contained or a layered structure having a plurality of layers in which these components are contained separately. Further, the recording material having an intermediate layer, as described in Japanese Patent Application No. 59-177669, and the heat-sensitive recording layer on a support.

Further, as it will be described later, a full color recording material in which a plurality of monochromic heat-sensitive recording layers with each different hue are layered can be used.

In the heat-sensitive recording material of the present invention, a binder may be added to the heat-sensitive recording layer, the intermediate layer, or the protection layer, which will be described later, and the binder may properly be selected from known water-soluble polymer compounds and latex.

The water-soluble polymer compounds are, for example, methyl cellulose, carboxymethyl cellulose, hydroxyethyl cellulose, hydroxypropyl cellulose, starch derivatives, casein, gum arabic, gelatin, an ethylene-maleic anhydride copolymer, a styrene-maleic acid anhydride copolymer, polyvinyl alcohol, a silanol-modified polyvinyl alcohol, a carboxy-modified polyvinyl alcohol, an epichlorohydrin-modified polyamide, isobutyrene-maleic anhydride copolymer, polyacrylic acid, a polyacrylic acid amide, and it modified products.

The latex is, for example, styrene-butadiene rubber latex, methyl acrylate-butadiene rubber latex, a vinyl acetate emulsion and the like.

Among them, hydroxyethyl cellulose, starch derivatives, gelatin, polyvinyl alcohol derivatives, polyacrylic acid amide derivatives are preferable.

Further, a pigment may be added to the heat-sensitive recording material of the invention and as the pigment, regardless of organic or inorganic, well-known pigments can be exemplified. For example, kaolin, calcined kaolin, talc, agalmatolite, kieselguhr, calcium carbonate, aluminum hydroxide, magnesium hydroxide, zinc oxide, lithopone, amorphous silica, colloidal silica, fired gypsum, silica, magnesium carbonate, titanium oxide, alumina, barium carbonate, barium sulfate, mica, microballoon, a urea-formalin filler, a polyester particle, a cellulose filler and the like can be exemplified.

Further, if necessary, it is also possible to use various additives such as known waxes, antistatic agents, defoaming agents, conductive agents, fluorescent dyes, surfactants, ultraviolet absorbers, and their precursors.

<Other layers>

On the heat-sensitive recording layer of the heat-sensitive recording material of the present invention, a protection layer may be formed. If necessary, two or more layers may be layered as the protection layer.

The materials used in the protection layer are water-soluble polymer compounds such as polyvinyl alcohol, a carboxy-modified polyvinyl alcohol, a vinyl acetate-acrylamide copolymer, a silicon-modified polyvinyl alcohol, starch, modified starch, methyl cellulose, carboxymethyl cellulose, hydroxymethyl cellulose, gelatins, gum arabic, casein, hydrolysates of a styrene-maleic acid copolymer, hydrolysates of a styrene-maleic acid copolymer half ester, hydrolysates of an isobuylene-maleic anhydride copolymer, polyacrylamide derivatives, polyvinyl pyrrolidone, sodium poly styrenesulfonate, sodium alginate and the like; and latex such as styrene-butadiene rubber latex, acrylonitrile-butadiene rubber latex, methyl acrylate-butadiene rubber latex, a vinyl acetate emulsion and the like.

The water-soluble polymer compound may be cross-linked to further improve the storage stability. As a cross-linking agent, known cross-linking agents can properly be selected and, for example, water-soluble initial condensation products such as N-methylol urea, N-methylol melamine, urea-formaline and the like; dialdehydes such as glyoxal, glutaraldehyde, and the like; inorganic cross-linking agents such as boric acid, borax, and the like; and polyamidoepichlorohydrine.

The protection layer may further contain a known pigment, a metallic soap, a wax, a surfactant or the like. Further, a known ultraviolet absorbent or a precursor thereof may be added.

The protection layer can be formed by applying a coating solution for forming a protection layer and the application amount is preferably 0.2 to 5 $g/m^2$, more preferably 0.5 to 2 $g/m^2$, on the basis of dried coating amount. The film thickness is preferably 0.2 to 5 $\mu$m and more preferably 0.5 to 2 $\mu$m.

The protection layer can be coated in the same manner that the heat-sensitive recording layer is coated on the support.

In the case in which the heat-sensitive recording material of the present invention is a full-color heat-sensitive recording material comprising a photo-fixing type heat-sensitive recording layers on the support, for the purpose of preventing color mixing among the heat-sensitive recording layers, an intermediate layer may be formed between the heat-sensitive recording layers.

The intermediate layer is composed of a water-soluble polymer compound such as gelatin, phthalic acid-modified gelatin, polyvinyl alcohol, polyvinylpyrrolidone and the like and may properly contain an additive.

In the case of a full-color heat-sensitive recording material, it is desirable to form a light transmittance adjustment layer and/or a protection layer may be formed on the heat-recording layer, if necessary. Details of the light transmittance adjustment layer are described in JP-A Nos. 9-39395, 9-39396, Japanese Patent Application Nos. 7-208386.

In the case in which a component working as a precursor of a ultraviolet absorbent is used in the light transmittance adjustment layer, since the component does not serve as the ultraviolet absorbent and the layer has a high light transmittance before radiation of light with wavelength in a region necessary for fixation, the layer can sufficiently transmit light with wavelength of a region necessary for fixing the photo-fixing type heat-sensitive recording layer and has a high transmittance of visible light and does not interfere the fixation of the heat-sensitive recording layer.

After radiation of the light with wavelength in the region necessary for photo-fixation (decomposition of the diazonium salt by light radiation) of the photo-fixing type heat-sensitive recording layer, the ultraviolet absorbent precursor is converted to an ultraviolet absorbent by the light. The ultraviolet absorbent absorbs almost all of the light with wavelength in the ultraviolet region and the transmittance of the light is decreased and then the lightfastness of the heat-sensitive recording material can be improved. However, since the ultraviolet absorbent scarcely absorbs visible light, the transmittance of the visible light is not changed.

At least one light transmittance adjustment layer may be formed in the heat-sensitive recording material and above all, it is preferably formed between the heat-sensitive recording layer and the protection layer. Further, one layer which serves as both the protection layer and the light transmittance adjustment layer can be formed.

<Support>

For a support usable for the heat-sensitive recording material of the present invention, any of common pressure sensitive paper and heat-sensitive paper, paper supports which is employed in dry type or wet type diazo copying paper and the like can be employed. In addition, acidic paper, neutral paper, coated paper, plastic film-laminated paper, synthetic paper, plastic films of such as polyethylene terephthalate, polyethylene naphthalate and the like can be employed.

For the purpose of correcting curl balance or for the purpose of improving the chemical-resistance of the rear side, a back coat layer may be formed on the support. The back coat layer can be formed in the same manner that the protection layer is coated.

Further, if necessary, an anti-halation layer may be formed between the support and the heat-sensitive recording layer or on the surface side of the support where the heat-sensitive recording layer is formed and a slip layer, an antistatic layer, an adhesive layer or the like may be formed on the rear side surface.

Further, the recording material is made in the form of a label by forming an adhesive layer on the rear side of the support (which rear side is opposite to the side of the support on which the recording layer is formed) and providing release paper on the adhesive layer.

As described above, addition of the diazonium salt of the invention to the heat-sensitive recording layer can give excellent color forming property and a high coloring density and the dye obtained from the diazonium salt has an excellent light resistance and then an image with good fastness can be obtained. Further, since the recording material of the present invention can be rapidly photo-fixed, the recording period can be shortened and moreover, since the diazonium salt itself easily decomposes, sufficient fixation effect can be expected. Accordingly, the deterioration of whiteness attributed to coloration of the non-image areas (the background areas) can be prevented and an image with scarce density alteration (excellent image storability) and a high contrast can be obtained.

Further, encapsulation of the diazonium salt in the microcapsules improves the stability (the raw storage property) of a recording material for a long time.

III. Image formation method

The image formation using the heat-sensitive recording material of the present invention may be carried out as follows.

For example, the surface of the heat-sensitive recording material on which surface the heat-sensitive recording layer is formed is heated imagewise by a heater such as a thermal head or the like, so that the capsule wall containing a polyurea and/or a polyurethane in the heated portions is softened to allow a substance to pass through the wall and then a coupler and a basic substance (an organic base) outside of the capsules enter the microcapsules and the coupler reacts with the diazonium salt to form color imagewise. In this case, after coloration, light with wavelength corresponding to the absorption wavelength of the diazonium salt is further radiated (photo-fixation) toward the recording material so as to cause decomposition of the diazonium salt and eliminate the reactivity thereof with the coupler, so that the image can be fixed. By carrying out photo-fixation as described above, the unreacted diazonium salt is decomposed and loses the activity, so that density alteration of the formed image and coloration in the non-image areas (the background areas) due to stain formation, that is, deterioration of the whiteness, and decrease of the image contrast due to the deterioration of the whiteness can be suppressed.

A light source to be employed for the photo-fixation may be a variety of fluorescent lamps, xenon lamps, mercury lamps, and the like and the emission spectra of these light source preferably approximately corresponds to the absorption spectrum of the diazonium salt in the heat-sensitive recording material from a viewpoint of fixation at a high efficiency.

Especially, in the present invention, it is more preferable to use a light source having the luminescence center wavelength of radiated light in a range from 350 to 430 nm.

Further, the heat-sensitive recording material may be used as a photo-writing heat development type heat-sensitive recording material for giving an image by forming a latent image with light and thermally developing the latent image to a visible image. In this case, printing and developing process is carried out by using a light source such as laser in place of a heater just as described above.

In the heat-sensitive recording material of the invention, a plurality of heat-sensitive recording layers with different hues are layered to form a multi-color heat-sensitive recording material. The heat-sensitive recording layers to be layered are heat-sensitive recording layers each containing a photo-decomposable diazonium salt.

Details of the multi-color heat-sensitive recording material are described in JP-A Nos. 3-288688, 4-135787, 4-144784, 4-144785, 4-194842, 4-247447, 4-247448, 4-340540, 4-340541, 5-34860, 5-194842, Japanese Patent Application No. 7-316280.

For example, the layer structure of the full-color heat-sensitive recording material may be as follows. However, the invention is not restricted to the following examples.

The full-color heat-sensitive recording material may have a layer structure which comprises two heat-sensitive recording layers (B layer and C layer) each having a diazonium salt with different photosensitive wavelength from each other in combination with a coupler capable of forming color with different hue by reaction with the counterpart diazonium salt when heated and a heat-sensitive recording layer (A layer) containing an electron-donating colorless dye and an electron-accepting compound, or the full-color heat-sensitive recording material may have a layer structure which comprises the above described two heat-sensitive recording layers (B layer and C layer) and a heat-sensitive recording layer (A layer) containing another different diazonium salt with photosensitive wavelength different from those of others and a coupler capable of forming color with different hue by reaction with the counterpart diazonium salt when heated.

More specifically, the full-color heat-sensitive recording material may have a layer structure which comprised a first heat-sensitive recording layer (A layer) containing a combination of an electron-donating colorless dye and an electron-accepting compound or a combination of a diazonium salt with the maximum absorption wavelength of less than 350 nm and a coupler which reacts with the diazonium salt when heated to form a first color; a second heat-sensitive recording layer (B layer) containing a diazonium salt with the maximum absorption wavelength of 360 nm±20 nm and a coupler which reacts with the diazonium salt when heated to form a second color; and a third heat-sensitive recording layer (C layer) containing a diazonium salt with the maximum absorption wavelength of 420 nm±20 nm and a coupler which reacts with the diazonium salt when heated to form a third color in that order from the support side.

In this case, full-color image recording can be formed by properly selecting the colors formed by the respective heat-sensitive recording layers to be three primary colors in subtractive coloration; yellow, magenta, and cyan.

The full-color recording material may be formed by laminating the respective recording layers of yellow, magenta, and cyan in any order, however in terms of the color reproducibility, it is preferable to form layers of yellow, cyan, and magenta or yellow, magenta, and cyan in this order from the support side.

In the case of the full-color heat-sensitive recording material, a recording method may be carried out as follows.

That is, at first, the third heat-sensitive recording layer (C layer) is heated to react the diazonium salt and the coupler contained in the layer. Next, the recording material is exposed to light with wavelength of 400±20 nm so as to decompose unreacted diazonium salt contained in the C layer. Then, the second heat-sensitive recording layer (B) is heated sufficiently to react the diazonium salt and the coupler contained in the layer. At that time, although the C layer is also intensely heated, the diazonium salt in the layer C has been already decomposed and has lost the coloring capability, so that further color is not formed in the C layer. After that, the recording material is exposed to light with wavelength of 360±20 nm to decompose the diazonium salt contained in the B layer. Finally, the first heat-sensitive recording layer (A) is heated sufficiently to form color. At that time, although the C layer and B layer are also intensely heated, the diazonium salts in these layers have been already decomposed and have lost the coloring capability, so that further color is not formed in these layers.

In the heat-sensitive recording material of the present invention is preferably the multi-color heat-sensitive recording material as described above.

As described above, the color formation mechanism of the heat-sensitive recording layer (A layer) directly disposed on the support is not restricted to the combination of an electron-donating dye and an electron-accepting dye or the combination of a diazonium salt and a coupler which reacts with the diazonium salt when heated, but may be color formation system using a basic compound and a compound which formes color when come into contact with the basic compound, a chelate type color forming system, and color forming system using a nucleophilic agent and a compound which elimination-reacts with the nucleophilic agent to form color. Another type of the full-color heat-sensitive recording material can be obtained by forming a heat-sensitive recording layer containing a diazonium salt and a coupler which reacts with the diazonium salt on such a heat-sensitive recording layer.

EXAMPLES

Hereinafter, examples of the present invention will be described, but the invention is not restricted to these examples.

Example 1

Synthesis of the exemplified compound A-2 8.6 g of 4-{[4-acetamido-3-(2-methylpropyloxy)phenyl]-(3-ethoxycarbonylpropyl)amino}butyric acid ethyl ester was dissolved in 30 ml of ethanol and 6.7 ml of concentrated hydrochloric acid was added thereto and the resulting solution was fluxed and heated for 2 hours. After that, the obtained reaction solution was cooled to 0° C., a solution containing 3 ml of water and 1.45 g of sodium nitrite was dripped into the reaction solution. After the reaction mixture was stirred at 10° C. for 1 hour, 4.6 g of potassium hexafluorophosphate was added to the reaction mixture and stirred at room temperature for 30 minutes.

15 ml of water was added to the resulting mixture to make crystal precipitate. The obtained crystal was collected by filtration, successively washed with water and isopropanol, and then recrystallized from ethyl acetate-isopropanol, and dried to obtain 5.2 g of the aimed compound (the exemplified compound A-2).

The obtained compound (a diazonium salt A-2) was identified by $^1$H-NMR (solvent: $CDCl_3$, 300 MHz). The data was as follows.

$^1$H-NMR ($\delta$, ppm): 7.88 (d, 1H), 6.86 (s, 1H), 6.78 (d, 1H), 4.14 (m, 6H), 3.60 (dt, 4H), 2.46 (dt, 4H), 2.18 (m, 1H), 1.12 (m, 4H), 1.28 (t, 6H), 1.04 (d, 6H).

Further, the maximum absorption wavelength ($\lambda$max) in acetone was 368 nm and the absorption coefficient was $3.7 \times 10^4$.

Example 2

Synthesis of the exemplified compound A-4 10.0 g of 4-{[4-acetamido-3-(3,5,5-trimethylhexyloxy)phenyl]-(3-ethoxycarbonylpropyl)amino}butyric acid ethyl ester was dissolved in 30 ml of ethanol and 6.5 ml of concentrated hydrochloric acid was added thereto and the resulting solution was fluxed and heated for 2 hours. After that, the obtained reaction solution was cooled to 0° C., a solution containing 3 ml of water and 1.42 g of sodium nitrite was dripped into the reaction solution. After the reaction mixture was stirred at 10° C. for 1 hour, 4.8 g of potassium hexafluorophosphate was added to the reaction mixture and stirred at room temperature for 1 hour. 15 ml of water was added to the resulting mixture to make crystal precipitate. The obtained crystal was collected by filtration, successively washed with water and isopropanol, and then recrystallized from ethyl acetate-isopropanol, and dried to obtain 6.1 g of the aimed compound (the exemplified compound A-4).

The obtained compound (a diazonium salt A-4) was identified by $^1$H-NMR (solvent: $CDCl_3$, 300 MHz). The data was as follows.

$^1$H-NMR ($\delta$, ppm): 7.88 (d, 1H), 6.86 (s, 1H), 6.78 (d, 1H), 4.41 (m, 2H), 4.14 (q, 4H), 3.60 (dt, 4H), 2.46 (m, 4H), 1.94 (m, 5H), 1.74 (m, 2H), 1.28 (t, 6H), 1.22 (dd, 2H), 1.02 (d, 3H), 0.92 (s, 9H).

Further, the maximum absorption wavelength ($\lambda$max) in acetone was 368 nm and the absorption coefficient was $4.0 \times 10^4$.

Example 3

Synthesis of the exemplified compound A-6 10.0 g of 4-{[4-acetamido-3-(1-methylheptyloxy)phenyl]-(3-ethoxycarbonylpropyl)amino}butyric acid ethyl ester was dissolved in 30 ml of ethanol and 6.7 ml of concentrated hydrochloric acid was added thereto and the resulting solution was fluxed and heated for 2 hours. After that, the obtained reaction solution was cooled to 0° C., a solution containing 3 ml of water and 1.46 g of sodium nitrite was dripped into the reaction solution. After the reaction mixture was stirred at 10° C. for 1 hour, 5.0 g of potassium hexafluorophosphate was added to the mixture and stirred at room temperature for 30 minutes. 15 ml of water was added to the resulting mixture to make crystal precipitate. The obtained crystal was collected by filtration, successively washed with water and isopropanol, and then recrystallized from ethyl acetate-isopropanol, and dried to obtain 6.1 g of the aimed compound (the exemplified compound A-6).

The obtained compound (a diazonium salt A-6) was identified by $^1$H-NMR (solvent: CDCl$_3$, 300 MHz). The data was as follows.

$^1$H-NMR ($\delta$, ppm): 7.88 (d, 1H), 6.82 (s, 1H), 6.78 (d, 1H), 5.04 (m, 1H), 4.14 (q, 4H), 3.58 (dt, 4H), 2.44 (dt, 4H), 1.94 (m, 4H), 1.62–1.90 (m, 4H), 1.20–2.42 (m, 15H), 0.88 (t, 3H).

Further, the maximum absorption wavelength ($\lambda$max) in acetone was 368 nm and the absorption coefficient was $3.9 \times 10^4$.

Example 4

Synthesis of the exemplified compound A-10 10.0 g of 4-{[4-acetamido-3-(3,5,5-trimethylhexyloxy)phenyl]-(3-methoxycarbonylpropyl)amino}butyric acid ethyl ester was dissolved in 30 ml of ethanol and 6.9 ml of concentrated hydrochloric acid was added thereto and the resulting solution was fluxed and heated for 3 hours. After that, the obtained reaction solution was cooled to 0° C., a solution containing 3 ml of water and 1.50 g of sodium nitrite was dripped into the reaction solution. After the reaction mixture was stirred at 10° C. for 1 hour, 5.1 g of potassium hexafluorophosphate was added to the mixture and stirred at room temperature for 1 hour. 15 ml of water was added to the resulting mixture to make crystal precipitate. The obtained crystal was collected by filtration, successively washed with water and isopropanol, and then recrystallized from ethyl acetate-isopropanol, and dried to obtain 6.6 g of the aimed compound (the exemplified compound A-10).

The obtained compound (a diazonium salt A-10) was identified by $^1$H-NMR (solvent: CDCl$_3$, 300 MHz). The data was as follows.

$^1$H-NMR ($\delta$, ppm): 7.88 (d, 1H), 6.86 (s, 1H), 6.78 (d, 1H), 4.41 (m, 2H), 3.68 (s, 6H), 3.60 (dt, 4H), 2.46 (m, 4H), 1.94 (m, 5H), 1.74 (m, 2H), 1.22 (dd, 2H), 1.02 (d, 3H), 0.92 (s, 9H).

Further, the maximum absorption wavelength ($\lambda$max) in acetone was 368 nm and the absorption coefficient was $3.9 \times 10^4$.

Example 5

Preparation of diazonium salt

The diazonium salt (exemplified compound A-2) of the present invention was synthesized in the same manner as that of the example 1.

Preparation of microcapsule solution $L_a$ encapsulating diazonium salt 4.1 g of the diazonium salt (exemplified compound A-2) thus obtained and 10 g of tricresyl phosphate were added to 19 g of ethyl acetate and uniformly mixed. Next, 7.6 g of Takenate D 110N (manufactured by Takeda Chemical Industries, Ltd.) as a capsule wall material was added to the mixed solution to obtain an solution I.

After that, the solution I thus obtained was added to a mixture of 46 g of an aqueous solution of 8% phthalic-modified gelatin, 17.5 g of water, and 2 g of an aqueous solution of 10% sodium dodecylbenzenesulfonate and emulsified at 40° C. at 10,000 rpm for 10 minutes by a homogenizer.

After 20 g of water was added to the obtained emulsion and mixed uniformly, microcapsulation reaction was carried out at 40° C. for 3 hours while stirring the mixture to obtain a microcapsule solution $L_a$ encapsulating the diazonium salt. The average particle diameter of the microcapsules was 0.8 to 1.0 μm.

Preparation of coupler emulsion $L_b$ 6.0 g of the coupler (exemplified compound B-42), 3 g of triphenyl guanidine, 0.5 g of tricresyl phosphate, and 0.24 g of diethyl maleate were dissolved in 10.5 g of ethyl acetate to obtain a solution II.

Next, the solution II thus obtained were added to a mixed solution obtained by uniformly mixing 49 g of an aqueous solution of 15% lime-treated gelatin, 9.5 g of an aqueous solution of 10% sodium dodecylbenzenesulfonate and 35 g of water and emulsified at 40° C. at 10,000 rpm for 10 minutes by a homogenizer.

After the obtained emulsified dispersion was stirred at 40° C. for 2 hours to remove ethyl acetate, water was supplemented to cover the evaporation amounts of ethyl acetate and water to obtain a coupler emulsion $L_b$.

Preparation of coating solution $L_c$ for heat-sensitive recording layer

A coating solution $L_c$ for a heat-sensitive recording layer was obtained by mixing 3.6 g of the microcapsule solution $L_a$ encapsulating the diazonium salt, 3.3 g of water, and 9.5 g of the coupler emulsion $L_b$.

Preparation of coating solution $L_d$ for protection layer 15 g of a dispersion of 40% zinc stearate (Hidorin Z, manufactured by Chukyo Yushi Co., Ltd.) was uniformly mixed to a mixed solution obtained by mixing 100 g of an aqueous solution of 6% itaconic acid-modified polyvinyl alcohol (Kl-318, manufactured by Kuraray Co., Ltd.) and 10 g of a dispersion of 30% epoxy-modified polyamide (FL-71, manufactured by Toho Chemical Industry Co., Ltd.) to obtain a coating solution $L_d$ for a protection layer.

Coating

As a support, a printing paper support of a high grade paper having thereon a polyethylene layer was prepared and the coating solution $L_c$ for a heat-sensitive recording layer and coating solution $L_d$ for a protection layer were successively applied to the surface of the printing paper support by a wire bar and the layers were dried (50° C.) to obtain the heat-sensitive recording material $M_1$ of the present invention. In this case, the solid matter application amounts of the heat-sensitive recording layer and the protection layer were 5.9 g/m$^2$ and 1.2 g/m$^2$, respectively.

Examples 6 to 8

Heat-sensitive recording materials $M_2$ to $M_4$ of the present invention were obtained in the same manner as Example 1, except that the exemplified compound A-4 (4.2 g), the exemplified compound A-6 (4.1 g), and the exemplified compound A-10 (4.0 g) were employed, respectively, in place of 4.1 g of the diazonium salt (the exemplified compound A-2) employed for preparation of the microcapsule solution $L_a$ encapsulating the diazonium salt of Example 1.

Comparative Examples 1 and 2

Heat-sensitive recording materials $M_5$ and $M_6$ of Comparative examples were obtained in the same manner as Example 1, except that 4.5 g of 4-bis (dibutylcarbamoylmethy)amino-2-(3-pentyloxy) benzenediazonium tetrafluorophosphate (the following compound 1) and 3.2 g of 4-dipropylaminoamino-2-(3,5,5-trimethylhexyloxy)benzenediazonium tetrafluorophosphate (the following compound 2) were used respectively in place of 4.1 g of the diazonium salt (the exemplified compound A-2) employed for preparation of the microcapsule solution $L_a$ encapsulating the diazonium salt of Example 1.

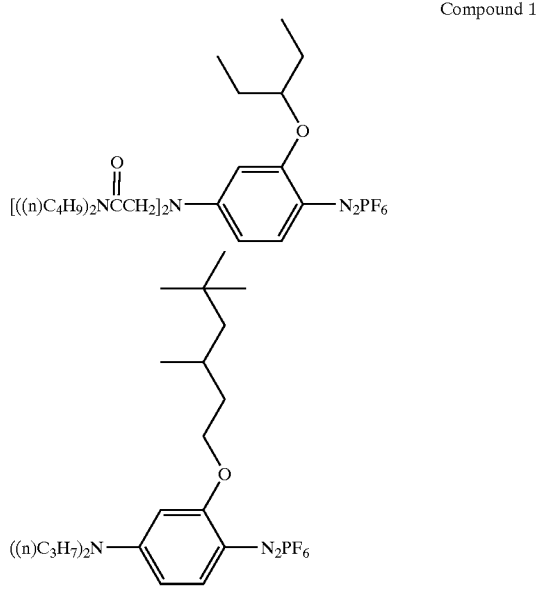

Compound 1

Measurement/Evaluation

Using the heat-sensitive recording materials $M_1$ to $M_4$ and the heat-sensitive recording materials $M_5$ to $M_6$ thus obtained, the following measurement and evaluation were carried out. The results of the measurement and the evaluation were shown in the Table 1.

[1] Evaluation of the color forming property and coloring density

Using a thermal head (KST model, manufactured by Kyocera Corporation), thermal printing was carried out on the heat-sensitive recording materials $M_1$ to $M_6$ by controlling the voltage applied to the thermal head and the pulse width so that the recording energy per unit surface area was 50 mJ/mm$^2$ and further ultraviolet rays were radiated for 15 seconds to the surface of each heat-sensitive recording layer where the image was formed using an ultraviolet lamp with a luminescence center wavelength of 450 nm and an output of 40 W.

Using a Mac-Bech densitometer (Reflection Densitometer RD 918, Mac-Bech Co.), the coloring density and the background density (the density of the non-image areas) were measured. The higher the coloring density was, the better coloring property was.

[2] Evaluation of the light-resistance (image storage property)

The image portions (the color forming portions) of each heat-sensitive recording material on which printing was carried out using the thermal head (KST model, manufactured by Kyocera Corporation) while the recording energy per unit surface area being controlled were exposed to light from a xenon lamp (85,000 lux, Atlas C. I 65, Weather O Meter, US Atlas Co.) for 24 hours and the remaining ratio (%) of the density after the radiation to the image density before radiation was calculated to use the ratio as an index for evaluation of the light-resistance.

[3] Evaluation of storage property (raw storage property)

The density (the fogging density) of non-image areas of the heat-sensitive recording materials $M_1$ to $M_6$ before and after storage for 72 hours under the conditions of 70° C. and relative humidity 30% were measured and the alteration degree of the fogging density of the non-image areas was obtained.

TABLE 1

Color forming property

| | coloring density | fogging density of non-image areas | Light-resitance density remaining ratio (%) | Storage property fogging density after storage |
|---|---|---|---|---|
| Example 5 | 2.4 | 0.077 | 93 | 0.113 |
| Example 6 | 2.4 | 0.075 | 93 | 0.111 |
| Example 7 | 2.5 | 0.079 | 93 | 0.111 |
| Example 8 | 2.5 | 0.077 | 93 | 0.112 |
| Comparative example 1 | 1.6 | 0.082 | 87 | 0.102 |
| Comparative example 2 | 2.5 | 0.077 | 90 | 0.127 |

From the results in Table 1, the heat-sensitive recording materials $M_1$ to $M_4$ containing the diazonium salts of the present invention as coloring components were found excellent in the coloring property and whiteness of the non-image areas (background portions) and formed images with a high contrast. Moreover, the whiteness of the non-image areas were not deteriorated even when storaged under high temperature and high humidity conditions, and the non-image portions had excellent storage capability (raw storage property) and the fixed image in the image areas were excellent in light-resitance and images with excellent light-fastness and storage property were formed.

On the other hand, in the case of the heat-sensitive recording materials $M_5$ using a diazonium salt having no di(alkoxycarbonylpropyl)amino group in 4-position, the coloring density was low and the light-resistance of the image areas was also inferior and in the case of the heat-sensitive recording materials $M_6$ using a diazonium salt having no branched alkoxy group in 2-position, raw storage property was inferior and the whiteness of the non-image areas could not be maintained.

What is claimed is:

1. A diazonium salt represented by the following general formula (1):

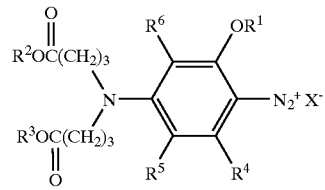

wherein $R^1$ represents a branched alkyl group; $R^2$ and $R^3$ separately represent an alkyl group and may bond to each other to form a ring; $R^4$, $R^5$, and $R^6$ separately represent a hydrogen atom, an alkyl group, or an aryl group and $R^4$ and $R^5$ may bond to each other to form a ring; and $X^-$ represents an anion.

2. A diazonium salt according to claim 1, represented by the following general formula (2):

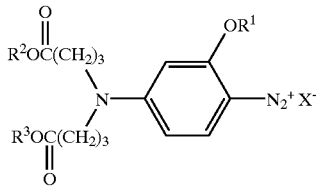

wherein $R^1$ represents a branched alkyl group; $R^2$ and $R^3$ separately represent an alkyl and may bond to each other to form a ring; and $X^-$ represents an anion.

3. A heat-sensitive recording material comprising a support and a heat-sensitive recording layer containing the diazonium salt according to claim 1 and a coupler.

4. A heat-sensitive recording material comprising a support and a heat-sensitive recording layer containing the diazonium salt according to claim 2 and a coupler.

5. A heat-sensitive recording material according to claim 3, wherein the coupler is a compound represented by the following general formula (3):

wherein $E^1$ and $E^2$ separately represent an electron attractive group and may bond with each other to form a ring.

6. A heat-sensitive recording material according to claim 4, wherein the coupler is a compound represented by the following general formula (3):

wherein $E^1$ and $E^2$ separately represent an electron attractive group and may bond with each other to form a ring.

7. A heat-sensitive recording material according to claim 5, wherein the coupler is a compound represented by the following general formula (4):

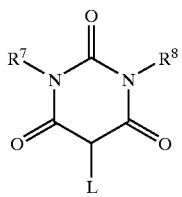

wherein $R^7$ and $R^8$ separately represent a hydrogen atom, an alkyl group, or an aryl group; and L represents a hydrogen atom or a substituent group capable of dissociating when the coupler is coupled with the diazonium salt.

8. A heat-sensitive recording material according to claim 6, wherein the coupler is a compound represented by the following general formula (4):

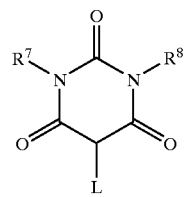

wherein $R^7$ and $R^8$ separately represent a hydrogen atom, an alkyl group, or an aryl group; and L represents a hydrogen atom or a substituent group capable of dissociating when the coupler is coupled with the diazonium salt.

9. A heat-sensitive recording material according to claim 3, wherein the heat-sensitive recording layer includes an organic base.

10. A heat-sensitive recording material according to claim 4, wherein the heat-sensitive recording layer includes an organic base.

11. A heat-sensitive recording material according to claim 5, wherein the heat-sensitive recording layer includes an organic base.

12. A heat-sensitive recording material according to claim 6, wherein the heat-sensitive recording layer includes an organic base.

13. A heat-sensitive recording material according to claim 3, wherein the diazonium salt is encapsulated in microcapsules.

14. A heat-sensitive recording material according to claim 4, wherein the diazonium salt is encapsulated in microcapsules.

15. A heat-sensitive recording material according to claim 5, wherein the diazonium salt is encapsulated in microcapsules.

16. A heat-sensitive recording material according to claim 6, wherein the diazonium salt is encapsulated in microcapsules.

17. A heat-sensitive recording material according to claim 13, wherein the microcapsules include a wall containing urethane and/or urea.

18. A heat-sensitive recording material according to claim 14, wherein the microcapsules include a wall containing urethane and/or urea.

19. A heat-sensitive recording material according to claim 15, wherein the microcapsules include a wall containing urethane and/or urea.

20. A heat-sensitive recording material according to claim 16, wherein the microcapsules include a wall containing urethane and/or urea.

* * * * *